US011185282B2

(12) United States Patent
Stenstrom et al.

(10) Patent No.: US 11,185,282 B2
(45) Date of Patent: Nov. 30, 2021

(54) SYSTEM AND METHOD FOR MONITORING AND IDENTIFYING POSOLOGY EFFICACY FOR AN AN INDIVIDUAL

(71) Applicant: APPMED INC., Laval (CA)

(72) Inventors: Philippe Stenstrom, Laval (CA); Louis-Paul Marin, Laval (CA)

(73) Assignee: APPMED INC., Laval (CA)

( * ) Notice: Subject to any disclaimer, the term of this patent is extended or adjusted under 35 U.S.C. 154(b) by 0 days.

(21) Appl. No.: 16/303,570

(22) PCT Filed: May 23, 2017

(86) PCT No.: PCT/CA2017/000133
§ 371 (c)(1),
(2) Date: Nov. 20, 2018

(87) PCT Pub. No.: WO2017/197492
PCT Pub. Date: Nov. 23, 2017

(65) Prior Publication Data
US 2020/0315528 A1    Oct. 8, 2020

Related U.S. Application Data

(60) Provisional application No. 62/339,419, filed on May 20, 2016.

(51) Int. Cl.
*A61B 5/00* (2006.01)
*G16H 50/30* (2018.01)
(Continued)

(52) U.S. Cl.
CPC .......... *A61B 5/4848* (2013.01); *A61B 5/0022* (2013.01); *A61B 5/0205* (2013.01);
(Continued)

(58) Field of Classification Search
CPC ... A61B 5/0022; A61B 5/0205; A61B 5/4833; A61B 5/4848; A61B 5/6801;
(Continued)

(56) References Cited

U.S. PATENT DOCUMENTS

| 7,698,157 | B2 * | 4/2010 | Ghouri | G16H 15/00 |
| | | | | 705/3 |
| 2004/0049506 | A1 * | 3/2004 | Ghouri | G16H 70/40 |

(Continued)

*Primary Examiner* — Jonathan T Kuo
(74) *Attorney, Agent, or Firm* — Praxis

(57) ABSTRACT

A system for monitoring and identifying the efficacy of posology for a target individual having a health condition with respect to administration of a therapeutic composition assigned thereto for treatment comprises a user interface, a database and a controller in communication with the user interface and the database. The database includes information of health conditions, symptoms, therapeutic compositions, and side effects. The controller comprises a memory of computer implementable steps for receiving information from the user interface regarding the target individual's health conditions, symptoms, therapeutic compositions and side effects assigned to the target individual; comparing the received information to a match with the health conditions, the therapeutic compositions, the symptoms and the side effects; prompting and receiving user feedback; and determining whether the therapeutic composition administered at a dosage should be modified to be increased or decreased.

13 Claims, 10 Drawing Sheets

Schema depicting user-application interaction in the application's posology system

(51) Int. Cl.
*G16H 50/70* (2018.01)
*G16H 70/40* (2018.01)
*G16H 80/00* (2018.01)
*A61B 5/0205* (2006.01)

(52) U.S. Cl.
CPC .......... *A61B 5/6801* (2013.01); *A61B 5/7465* (2013.01); *G16H 50/30* (2018.01); *G16H 50/70* (2018.01); *G16H 70/40* (2018.01); *G16H 80/00* (2018.01)

(58) Field of Classification Search
CPC ...... A61B 5/7455; G16H 40/67; G16H 50/30; G16H 50/70; G16H 70/40; G16H 80/00
See application file for complete search history.

(56) References Cited

U.S. PATENT DOCUMENTS

| | | | |
|---|---|---|---|
| 2008/0194924 A1* | 8/2008 | Valk | A61B 5/02007 600/301 |
| 2014/0108026 A1* | 4/2014 | Gale | G16H 20/40 705/2 |
| 2015/0088540 A1* | 3/2015 | Lo | G16H 70/40 705/2 |
| 2015/0193597 A1* | 7/2015 | Cederlund | G16H 70/40 705/2 |

* cited by examiner

FIGURE 3. Schema depicting user-application interaction in the application's posology system FIGURE 4. An illustration of how posology variables and the posology intervals comprise the final randomised titration schedule.

FIGURE 5. The Titration System

FIGURE 6. Relationships between individuals, accounts and dossiers

FIGURE 7. Schema depicting user-application interactions in the application's communication system FIGURE 8. Schema depicting user-application interactions in the application's communication system FIGURE 9. Use of data to predict treatment outcomes.

SYSTEM AND METHOD FOR MONITORING AND IDENTIFYING POSOLOGY EFFICACY FOR AN AN INDIVIDUAL

CROSS-REFERENCE TO RELATED APPLICATIONS

The present application claims priority on U.S. Provisional Patent Application No. 62/339,419 filed on May 20, 2017 and incorporated herein by reference in its entirety.

TECHNICAL FIELD

The present disclosure relates to a system and method for monitoring and identifying posology efficacy for an individual. More particularly, but not exclusively, the present disclosure relates to system end method for assisting a health professional or researcher in identifying optimal posology for an individual and to provide communication and coordination between actors in the context of a medical or mental health condition.

BACKGROUND

The efficiency end side effects of medication are variable from person to person, as are the symptoms of a given health issue. There are currently limited methods for monitoring symptoms and side-effects of medication and/or therapy in a longitudinal manner, and no product on the market collects and analyses information specifically for comparing several posologies or treatments in a single individual.

Objects

An object of the present disclosure is to provide a system for monitoring and identifying posology efficacy for an individual.

An object of the present disclosure is to provide a method for monitoring and identifying posology efficacy for an individual.

SUMMARY

In accordance with an aspect of the present disclosure, there is provided a system for monitoring and identifying the efficacy of posology for a target individual having a health condition with respect to administration of a therapeutic composition assigned to the target individual for treatment of the health condition, the system comprising: a user interface for being accessed by a user; a database of: a plurality of health conditions, a plurality of symptoms indicative of respective ones of the plurality of health conditions, a plurality of therapeutic compositions for treating respective ones of the plurality of health conditions, a plurality of side effects associated to respective ones of the plurality of the therapeutic compositions; and a controller in communication with the user interface and with the database, the controller comprising a memory of computer implementable steps for: receiving information from the user interface regarding the target individual's health condition and comparing this information to the database to match this information to at least one of the plurality of health conditions in the database thereby providing a matched condition and identifying one or more of the plurality of symptoms in the database indicative of the matched condition thereby providing identified symptoms; receiving information from the user interface regarding the therapeutic composition assigned to the target individual, comparing this information to the database to match this information to at least one of the plurality of therapeutic compositions in the database thereby providing a matched therapeutic composition, and Identifying one or more of the plurality of side effects in the database associated with the matched therapeutic composition thereby providing identified side effects; prompting and receiving user feedback via the user interface regarding the possibility of the target individual manifesting the identified symptoms or the identified side effects; determining based on the user feedback whether the therapeutic composition assigned to the target individual is administered at a dosage that should be modified in order to be increased or decreased, wherein manifestation of identified symptoms is indicative of a dosage that should be increased and manifestation of identified side effects is indicative of a dosage that should be decreased.

In accordance with an embodiment of the system, the database further comprises a databank of information related to a plurality of previous target individuals, wherein the information related to the plurality of previous target individuals comprises the health conditions and related symptoms of the plurality of previous target individuals, the therapeutic compositions assigned the plurality of previous target individuals in treatment of the health conditions of the plurality of previous target individuals, and the side effects of therapeutic compositions assigned to the plurality of previous target individuate. In accordance with an embodiment of the system, the memory of computer implemented steps further comprises statistically modifying the plurality of symptoms in the database end the plurality of side effects in the database in accordance with the information related to the plurality of the previous target individuals. In accordance with an embodiment of the system, the information related to the plurality of previous target individuals further comprises identifiers associated with respective ones of the plurality of target individuals thereby providing previous identifiers. In accordance with an embodiment of the system, the memory of computer implemented steps further comprises: receiving information from the user interface regarding the target individual's Identifiers and comparing this information to the previous identifiers to assess similarities therebetween thereby providing common identifiers; identifying the previous target individuals with the common identifiers and with the matched condition and matched therapeutic composition thereby providing common previous target individuals; identifying the symptoms of the common previous target individuals for the matched condition thereby providing common symptoms and identifying the side effects of the common previous target individuals for the matched therapeutic composition thereby providing common side effects; prompting and receiving user feedback via the user interface regarding the possibility of the target individual manifesting the common symptoms or the common side effects; determining based on the user feedback whether the therapeutic composition assigned to the target individual is administered at a dosage that should be modified in order to be increased or decreased, wherein manifestation of common symptoms is indicative of a dosage that should be increased and manifestation of common side effects is indicative of a dosage that should be decreased.

In accordance with an embodiment of the system, the database further comprises a plurality of predetermined posology ranges related to the administration of respective ones of the plurality of the therapeutic compositions for treating respective ones of the plurality of health conditions, wherein the memory further comprises the computer implemented steps of: receiving information via the user interface regarding a prescribed posology for the target individual and comparing this information to the plurality of posology ranges for the matched therapeutic composition in treating the matched health condition thereby identifying a predetermined posology range for the target individual; comparing the prescribed posology range with the predetermined posology range to identify discrepancies therebetween; and determining based on the user feedback and on the identified discrepancies whether the prescribed posology range should be modified to remove the identified discrepancies, wherein manifestation of identified symptoms or identified side effects is indicative of a prescribed posology range that should be modified. In accordance with an embodiment of the system, the database further comprises a databank of information related to a plurality of previous target individuals, wherein the information related to the plurality of previous target individuals comprises plurality of previous posology ranges related to the administration of respective ones of the plurality of the therapeutic compositions for treating respective ones of the plurality of health conditions. In accordance with an embodiment of the system, the memory of computer implemented steps further comprises statistically modifying the plurality of predetermined posology ranges in the database in accordance with the information related to the plurality of the previous target individuals. In accordance with an embodiment of the system, the information related to the plurality of previous target individuals further comprises identifiers associated with respective ones of the plurality of target individuals thereby providing previous identifiers. In accordance with an embodiment of the system, the memory of computer implemented steps further comprises: receiving information from the user interface regarding the target individual's identifiers and comparing this information to the previous identifiers to assess similarities therebetween thereby providing common identifiers; identifying the previous target individuals with the common identifiers and with the matched condition and matched therapeutic composition thereby providing common previous target individuals; processing the posology ranges of the common previous target individuals to provide a statistically common posology range; comparing the prescribed posology range with the statistically common posology range to identify discrepancies therebetween; and determining based on the user feedback and on the identified discrepancies whether the prescribed posology range should be modified to remove the identified discrepancies, wherein manifestation of identified symptoms or identified side effects is indicative of a prescribed posology range that should be modified.

In accordance with an embodiment of the system, the memory of computer implementable steps further comprises transmitting the determined modification to the user interface.

In accordance with an embodiment of the system, the user interface is configured to be used by a user selected from the group consisting of: the target individual, one or more physician, one or more monitor and a combination thereof.

In accordance with an embodiment, the system further comprises one or more additional user interfaces, wherein the one or more additional user interfaces are respectively configured to display predetermined information regarding the target individual as selectively programmed to be transmitted by the controller.

In accordance with an embodiment, the system further comprises biosensors mounted to the target individual and in communication with the controller directly or vie the user interface for providing the controller with information detected by the biosensors. In accordance with an embodiment of the system, the information detected by the biosensors comprises: one or more symptoms, one or more side effects, one or more identifiers and a combination thereof.

In accordance with an aspect of the present disclosure, there is provided a method for monitoring and identifying the efficacy of posology for a target individual having a health condition with respect to administration of a therapeutic composition assigned to the target individual for treatment of the health condition, the method comprising: providing a database of: a plurality of health conditions, a plurality of symptoms indicative of respective ones of the plurality of health conditions, a plurality of therapeutic compositions for treating respective ones of the plurality of health conditions, a plurality of side effects associated to respective ones of the plurality of the therapeutic compositions; receiving information regarding the target individual's health condition; automatically comparing this information in real-time to the database to match this information to at least one of the plurality of health conditions in the database thereby automatically providing in real-time a matched condition; automatically identifying in real-time one or more of the plurality of symptoms in the database indicative of the matched condition thereby providing identified symptoms; receiving information from the user interface regarding the therapeutic composition assigned to the target individual; automatically comparing this information in real-time to the database to match this information to at least one of the plurality of therapeutic compositions in the database thereby providing a matched therapeutic composition; automatically Identifying in real-time one or more of the plurality of side effects in the database associated with the matched therapeutic composition thereby providing identified side effects; prompting and receiving user feedback regarding the possibility of the target individual manifesting the identified symptoms or the identified side effects; automatically determining in real-time based on the user feedback whether the therapeutic composition assigned to the target individual is administered at a dosage that should be modified in order to be increased or decreased, wherein manifestation of identified symptoms is indicative of a dosage that should be increased and manifestation of identified side effects is indicative of a dosage that should be decreased.

In accordance with an embodiment of the method, the database further comprises a databank of information related to a plurality of previous target individuals, wherein the information related to the plurality of previous target individuals comprises the health conditions and related symptoms of the plurality of previous target individuals, the therapeutic compositions assigned the plurality of previous target individuals in treatment of the health conditions of the plurality of previous target individuals, and the side effects of therapeutic compositions assigned to the plurality of previous target individuals. In accordance with an embodiment, the method further comprises: automatically statistically modifying the plurality of symptoms in the database and the plurality of side effects in the database in accordance with the information related to the plurality of the previous target individuals. In accordance with an embodiment of the method, the information related to the plurality of previous target individuals further comprises identifiers associated with respective ones of the plurality of target individuals thereby providing previous identifiers. In accordance with an embodiment, the method further comprises: receiving information regarding the target individual's identifiers; automatically comparing in real-time the information regarding the target individual's identifiers to the previous identifiers to assess similarities therebetween thereby providing common identifiers; automatically identifying in real-time the previous target individuals with the common identifiers and with the matched condition and matched therapeutic composition thereby providing common previous target individuals; automatically identifying in real-time the symptoms of the common previous target individuals for the matched condition thereby providing common symptoms; automatically identifying in real-time the side effects of the common previous target individuals for the matched therapeutic composition thereby providing common side effects; prompting and receiving user feedback regarding the possibility of the target Individual manifesting the common symptoms or the common side effects; automatically determining in real-time based on the user feedback whether the therapeutic composition assigned to the target individual is administered at a dosage that should be modified in order to be increased or decreased, wherein manifestation of common symptoms is indicative of a dosage that should be increased and manifestation of common side effects is indicative of a dosage that should be decreased.

In accordance with an embodiment of the method, the database further comprises a plurality of predetermined posology ranges related to the administration of respective ones of the plurality of the therapeutic compositions for treating respective ones of the plurality of health conditions, the method further comprising: receiving Information regarding a prescribed posology for the target individual; automatically comparing in real-time this information to the plurality of posology ranges for the matched therapeutic composition in treating the matched health condition thereby identifying a predetermined posology range for the target individual; automatically comparing in real-time the prescribed posology range with the predetermined posology range to identify discrepancies therebetween; and automatically determining in real-time based on the user feedback and on the identified discrepancies whether the prescribed posology range should be modified to remove the identified discrepancies, wherein manifestation of identified symptoms or identified side effects is indicative of a prescribed posology range that should be modified. In accordance with an embodiment of the method, the database further comprises a databank of information related to a plurality of previous target individuals, wherein the information related to the plurality of previous target individuals comprises plurality of previous posology ranges related to the administration of respective ones of the plurality of the therapeutic compositions for treating respective ones of the plurality of health conditions. In accordance with an embodiment, the method further comprises statistically modifying the plurality of predetermined posology ranges in the database in accordance with the information related to the plurality of the previous target individuals. In accordance with an embodiment of the method, the information related to the plurality of previous target individuals further comprises identifiers associated with respective ones of the plurality of target individuals thereby providing previous identifiers. In accordance with an embodiment, the method further comprises: receiving information regarding the target individual's identifiers; automatically comparing in real-time the information regarding the target individual's identifiers to the previous identifiers to assess similarities therebetween thereby providing common identifiers; automatically identifying in real-time the previous target individuals with the common identifiers and with the matched condition and matched therapeutic composition thereby providing common previous target individuals; automatically processing in real-time the posology ranges of the common previous target individuals to provide a statistically common posology range; automatically comparing in real-time the prescribed posology range with the statistically common posology range to identify discrepancies therebetween; and automatically determining in real-time based on the user feedback and on the identified discrepancies whether the prescribed posology range should be modified to remove the identified discrepancies, wherein manifestation of identified symptoms or identified side effects is indicative of a prescribed posology range that should be modified.

In an embodiment, the method further comprises automatically transmitting in real time the determined modification to a user. In an embodiment of the method, the user is selected from the group consisting of: the target individual, one or more physician, one or more monitor and a combination thereof.

In an embodiment, the method further comprises automatically transmitting in real time to one or a plurality of selectively predetermined information regarding the target individual.

In an embodiment, the method further comprises: mounting biosensors the target individual; and receiving in real-time information detected by the biosensors. In an embodiment of the method, the information detected by the biosensors comprises: one or more symptoms, one or more side effects, one or more identifiers and a combination thereof.

Other objects, advantages and features of the present disclosure will become more apparent upon reading of the following non-restrictive description of illustrative embodiments thereof, given by way of example only with reference to the accompanying drawings.

DETAILED DESCRIPTION OF ILLUSTRATIVE EMBODIMENTS

Figure 1:
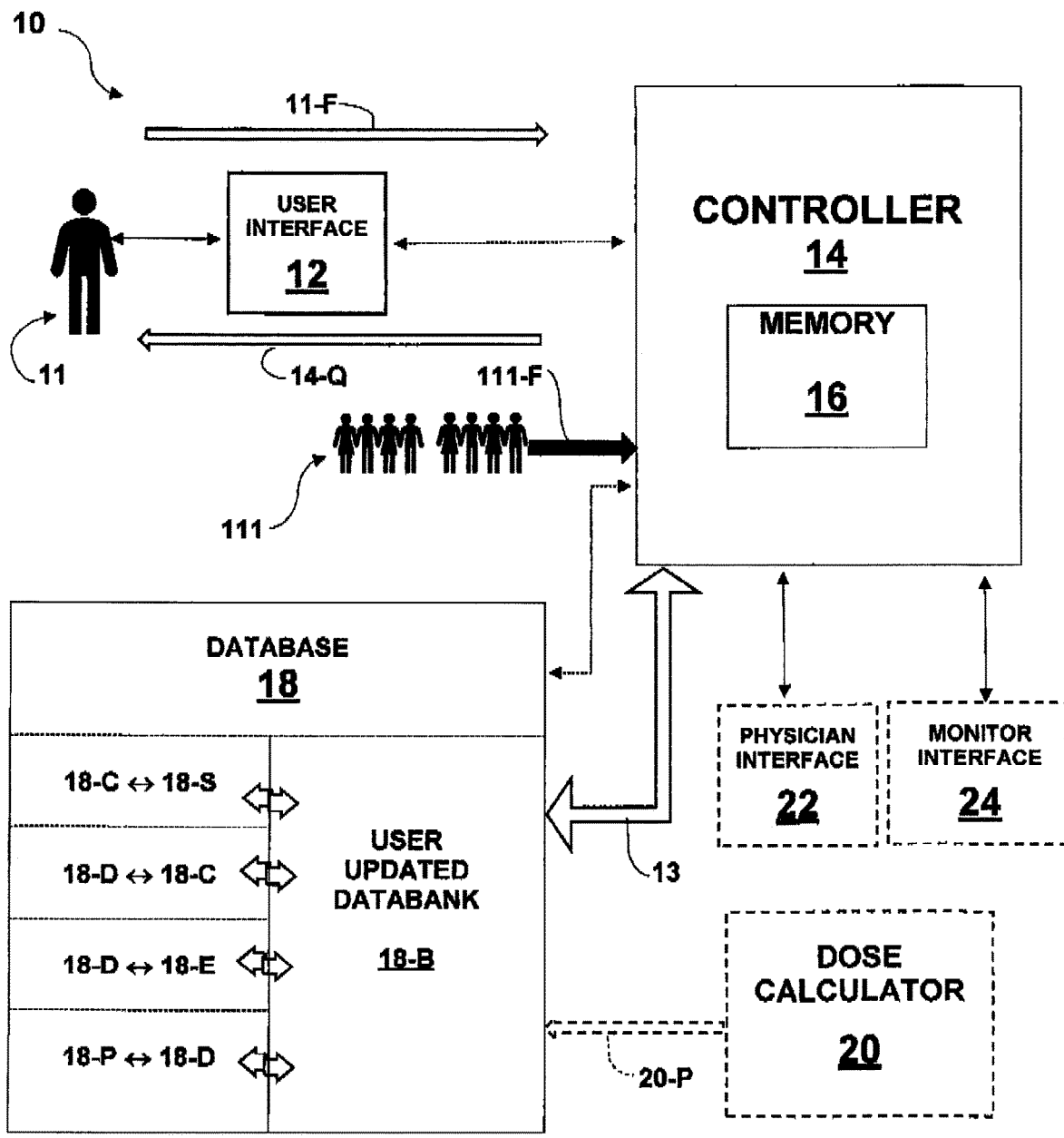
FIG. 1 is a schematic representation of a system for monitoring and identifying posology efficacy for an individual in accordance with a non-restrictive Illustrative embodiment of the present disclosure.

Generally stated and in accordance with an aspect of the present disclosure, there is provided a system for monitoring and identifying the efficacy of posology for a target individual having a health condition with respect to administration of a therapeutic composition assigned to the target individual for treatment of the health condition. The system comprises a user interface for being accessed by a user, a database and a controller in communication with the user interface and the database. The database includes pluralities of health conditions, of therapeutic compositions for treating these health conditions, and of side effects associated to these therapeutic compositions. The controller comprises a memory of computer implementable steps. The controller receives information from the user interface regarding the target Individual's health condition and the therapeutic composition assigned to the target individual. The received information is compared to the database provide a match with at least one of the plurality of health conditions in the database thereby providing a matched condition and to provide a match with at least one of the plurality of therapeutic compositions in the database thereby providing a matched therapeutic composition. The symptoms of the matched condition are identified providing identified symptoms. The side effects of the matched therapeutic compositions are identified thereby providing identified side effects. The controller prompts and receives user feedback regarding the possibility of the target individual manifesting the identified symptoms or the identified side effects. Based on the user feedback, the controller determines whether the therapeutic composition assigned to the target individual is administered at a dosage that should be modified in order to be increased or decreased. Manifestation of identified symptoms is indicative of a dosage that should be increased and manifestation of identified side effects is indicative of a dosage that should be decreased.

Generally stated and in accordance with an aspect of the present disclosure, there is provided a method for monitoring and identifying the efficacy of posology for a target individual having a health condition with respect to administration of a therapeutic composition assigned to the target individual for treatment of the health condition. The method comprises: providing a database pluralities of health conditions, of therapeutic compositions for treating these health conditions, and of side effects associated to these therapeutic compositions; receiving information regarding the target individual's health condition; automatically comparing this information in real-time to the database to match this information to at least one of the plurality of health conditions in the database thereby automatically providing in real-time a matched condition; automatically identifying in real-time one or more of the plurality of symptoms in the database indicative of the matched condition thereby providing identified symptoms; receiving information from the user interface regarding the therapeutic composition assigned to the target individual; automatically comparing this information in real-time to the database to match this information to at least one of the plurality of therapeutic compositions in the database thereby providing a matched therapeutic composition; automatically identifying in real-time one or more of the plurality of side effects in the database associated with the matched therapeutic composition thereby providing identified side effects; prompting and receiving user feedback regarding the possibility of the target individual manifesting the identified symptoms or the identified side effects; automatically determining in real time based on the user feedback whether the therapeutic composition assigned to the target individual is administered at a dosage that should be modified in order to be increased or decreased, wherein manifestation of identified symptoms is indicative of a dosage that should be increased and manifestation of identified side effects is indicative of a dosage that should be decreased.

The system prompts the user (including other actors, such as parents or spouses) to collect symptom and side-effect data in a systematic and responsive manner, and displays the collected data in a number of formats specifically designed to assist users, health professionals and other actors to make health and treatment-related decisions. Several prescriptions or treatments can be compared in a single user during a titration period to determine optimal posology or treatment; the logistics (e.g., scheduling and interaction with the participating pharmacy) is handled by the application that also provides a method of systematically collecting and reporting longitudinal medication efficiency and side effects. The application also provides a communication platform so that data collection can be done in a systematic, interactive and coordinated manner across a large number of actors.

The present disclosure helps minimize the undesirable effects of a medical or mental health condition, including drug withdrawal. It achieves this via two interrelated but standalone systems: 1) a system assisting a health professional or researcher in identifying optimal posology for an individual (posology system) and 2) a system providing communication and coordination between a person with a medical or mental health condition and individuals involved with its treatment (communication system). In an embodiment, the application is intended for interface devices such as smartphones mobiles, tablets, personal computers and the like.

In an embodiment, the present posology system is used to establish optimal posology for medication that an individual is currently taking or will be taking. Optimal posology is defined as the most efficient timing (when to take the medication), type (what type of medication to take, if several medications are available for a particular condition, and suitable for a particular individual) and the amount (typically in mg) of medication to achieve the most benefits from the medication while avoiding the most of its disadvantages (e.g., side effects), in an embodiment, this is done by prompting and allowing for systematic evaluations of the medication's benefits and disadvantages, and by subsequently analysing and displaying this feedback to assist a prescribing physician in adjusting or initiating a prescription. The disclosure also uses a system (i.e., titration system) to examine the effects of several different posologies, so that they may be compared in a systematic and objective manner akin to a double blind clinical study (albeit with a single participant).

In an embodiment, several individuals (users) use the present system and method in order to establish en optimal posology for a single individual (target individual). Users can be, but are not limited to, relatives, teachers, social workers, psychologists, lawyers, and health professionals. These individuals use the application to communicate data that will be used to establish optimal posology for the target individual. In an embodiment, the application requires at least a target individual and a prescribing physician (or researcher). The target individual may also be a user. In addition to being used in a physician-patient setting, the application can be used for research uses (e.g., determining the effects of drugs under development).

Each user has a unique instance of the application on their user device (e.g., mobile, desktop computer, etc.); the different users are linked together via an internet connection and a centralized server. The users' applications are linked insofar as they are used with regards to a single medicated-individual. The interface of the application is dependent upon the relationship between the user and the medicated-Individual. For example, the medicated-individual's parent has a parent account that displays information and functionalities that is relevant to parents, while the medicated-individual's physician has a physician account that provides information and functionalities pertinent to a health care professional.

Figure 2:
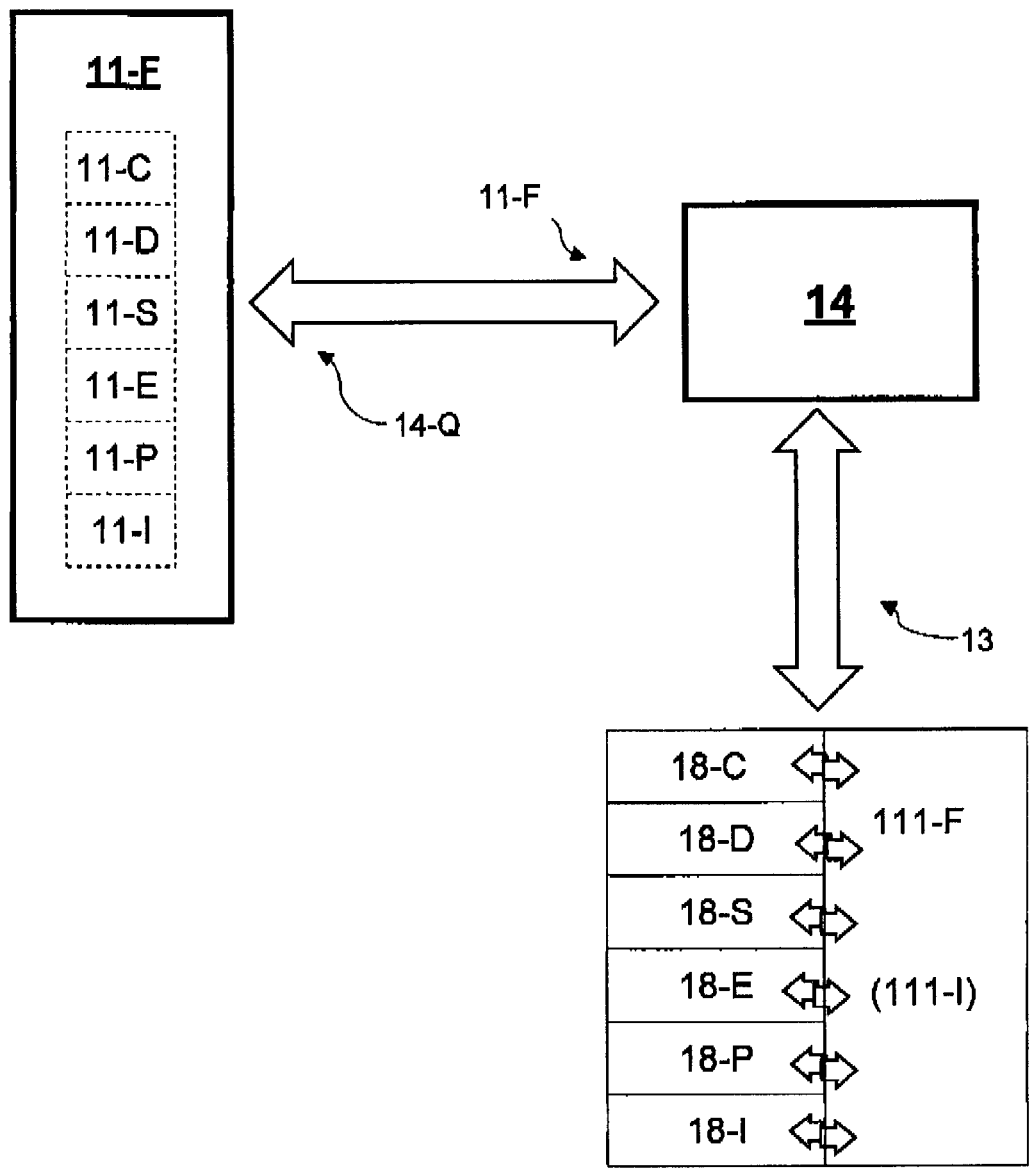
FIG. 2 is a schematic representation of the communication between the controller and both the user interface and the database of the system of FIG. 1, in accordance with a non-restrictive illustrative embodiment of the present disclosure.

Turning now to FIGS. 1 and 2, a non-restrictive illustrative embodiment of the present system and method will be discussed.

FIG. 1 shows the system 10 for identifying optimal posology of an Individual 11 having a condition such as a medical or mental health condition. The system 10 includes a user interface 12 for being accessed by the individual 11 as will be explained hereinbelow. The user interface 12 is in communication with a remote controller 14 such as a server for example. The controller 14 includes a memory 16 of computer implementable steps and is in communication with a database 18.

The database 18 comprises information related to a plurality of conditions 18-C including the symptoms 18-S of these conditions 18-C, the therapeutic compositions 18-D related to the treatment of these conditions 18-C as well as the side effects 18-E of these therapeutic compositions 18-D.

In an embodiment, the database 18 comprises information related to an average posology 18-P for a given therapeutic composition 18-D. This average posology 18-P is based on clinical data averages known in the art.

In another embodiment, the database 18 is in communication with a dose calculator 20 that provides information thereto regarding the posology 20-P of the therapeutic compositions 18-D for treating conditions 18-C. The posology 20-P provided by the dose calculator 20 is based on clinical data averages and provides a dosage range and temporal schedule for a given therapeutic composition 18-D to treat a given condition 18-C of an individual based on the individual's profile as compared to the clinical data averages.

Examples of dose calculators include without limitation, the system and methodology published by Guillame Bonnefois, Développement d'algorithmes d'individualisation TDAH et don implementation en une application interactive, Université de Montréal-Faculté de Pharmacia, 6 Dec. 2013, which is incorporated herein in its entirety.

In an embodiment, the posology 20-P is communicated to the database 18 directly or via the controller 14. In an embodiment, the average posology 18-P is readjusted in accordance with 20-P. In an embodiment, the average posology 18-P is replaced by 20-P end thus the dose calculator 20 is the database 18. In one embodiment, the database provided herein is a combined unit of database 18 and dose calculator 20. In one embodiment, the database herein is a hybrid unit of the database 18 and dose calculator 20.

In one embodiment, the clinical averages provided by the database 18 and/or dose calculator 20 also considers the temporal range of administration of the therapeutic composition and not only the dose range. Therefore, posology averages are a function of dose of administration and time of administration. In one example, this dosage-temporal average is assigned an efficacy score based on absence of symptoms and absence of side effects. In an embodiment, this efficacy score is also a function of other identifiers of groups or categories of individuals such as age, location, height, weight, location, activity, habits, general health including having other medical or mental health conditions, consumption of other therapeutic compositions end even sociological and psychological factors.

In one example, the individual 11 inputs data 11-F via the user interface 12 regarding their condition (as determined by their physician), the therapeutic composition(s) they are consuming as or the treatment provided by their physician, and other required identifier or classification information such as age, gender, weight and the like which is required by the dose calculator 20 to provide a range based on the clinical data averages for a given group classification of individuals, for example, one group Z may consist of: individuals suffering from condition X consisting of males between the ages of 35-45, having a Body Mass Index of between 25-30, and a sedentary lifestyle. In one example, condition X is treated by composition Y, the dose calculator 20 contains clinical averages data regarding the efficacy score of Y based on both dose and time of administration for group X. If the individual fits the profile identifiers of group Z, then the controller 14 retrieves this information from the dose calculator 20 and the initial posology 20-P is retrieved.

The initial posology 18-P or 20-P provided by the system 10, is often quite long and burdensome for the physician to sift through it via a long titration process in order to uncover the optimal dosage for the individual 11.

The system 10 provides for further narrowing down the initial posology 18-P or 20-P in order to identify the optimal posology for the individual 11.

The database 18 includes a data bank 18-B of users populated by various individuals 111 who have already uncovered their optimal posology via the computer implementable steps provided herein and the subsequent titration process explained further below. In this way, the controller 14 compares the information 11-F received by the individual as will be further explained below with the information 111-F received by the plurality of individuals and stored in the data bank 18-B. It should be noted that the data bank 18-B is updated in real time by a plurality of users 111 of the system 10. Therefore, the data bank 18-B is being modified in real time by the plurality of user feedback 111-F as will be further exemplified below.

As such, an individual's feedback 11-F (including identifiers such es profile) will be compared to the accumulated feedback 111-F (including identifiers such as profiles) of the data bank 18-B having the same condition 18-C as the individual 11 and using the same therapeutic composition 18-D as the individual 11. Accordingly, the controller 14 will identifies a sub-range within the initial range 18-P or 20-P, based on the similarity of the individual's profile 11-F with the accumulated profiles 111-F of the data bank 18-B.

The individual's profile 11-F is based not only on identifiers (11-I, see FIG. 2) such as age, gender, location, height, weight, habits, general health and the like but on feedback assessed in a longitudinal manner and accumulated by the controller 14. The individual's feedback 11-F is prompted 14-Q by the controller 14 via the user interface 12, over several days (one or more times a day) which requests symptom specific (to the individual's condition) and side effect specific (to the therapeutic composition) information from the individual 11. In posology, there are two general thresholds: if the dose is too low, the individual will experience symptoms of the condition and if the dose it too high the individual will experience side effects of the therapeutic composition used to treat the condition. Thus, the goal is to find the optimal dosage having the greatest efficacy while substantially avoiding the side effects between these two thresholds. Moreover, other factors may influence the efficacy of the therapeutic composition such as the time of day of administration and other general health conditions. The efficacy is also a function of a variety of other factors related to the individual 11 (age, weight, height, general health, consumption of other therapeutic compositions etc,), Therefore, the individual's dosage, symptoms, side effects, identifiers (11-F/11-I) will be compared to the accumulated profiles, generally denoted as 111-F (including 111-I, see FIG. 2). More specifically, the longitudinally assessed individual's profile 11-F is compared in real time to the accumulated profiles 111-F which Includes feedback assessed in a similar fashion as that of the individual 11. The goal of the comparison between 11-F and 111-P is to identify a smaller dosage sub-range of 16-P (or 20-P as discussed above). If the sub-range is determined to be too large by the controller 14 based on predetermined parameters (such as providing a less cumbersome titration process), the controller 14 continues to request further symptom specific and side effect specific information (14-Q) on the basis of the foregoing comparison (13) to further narrow down the dosage range until a resulting dosage range is provided that meets the predetermined parameters of the controller 14. In an embodiment, these predetermined parameters comprise a titration program of a preferred maximum set of days that provides for determining the optimal posology as will be further discussed below.

In one embodiment, the controller 14 implements the step of Identifying the highest efficacy score (as discussed above) for an individual 11 based on the closest similarity between 11-F and 111-F.

In an embodiment, once the above iteration process is complete (the Iteration process comprising several rounds of prompting 14-Q, feedback 11-F and comparison 13), the resulting dosage range is reported to the physician of the individual 11 via a physician interface 22 and a titration program is set up within the resulting dosage range. In one example, the physician provides a kit to the individual with a dosage protocol to be followed for several days to identify the optimal posology for the Individual within the provided resulting dosage range.

The physician informs the controller 14 of the titration program. During the titration program, the controller 14 effectuates a second iteration process by continuing to monitor the individual 11 by prompting (14-Q) the individual 11 to respond (11-F) to symptom specific and side effect specific questions in order to identify the optimal posology within the dosage range of the titration program and report same to the physician thereby setting the optimal dosage.

With reference to both FIGS. 1 and 2, the controller 14 receives via the interface 12 the individual's basic information (11-F) including their condition, (11-C) the therapeutic composition (11-D) and dosage (11-P) thereof that they have been prescribed as well as other identifiers (11-I) (e.g. gender, age, weight, height, BMI, activity, general health questions etc).

The controller 14 implements a series of iteration steps based on the information 11-F it has received from the individual 11 in comparison 13 to the information of the database 18.

Accordingly, the controller 14 compares 13 an individual's condition 11-C, the therapeutic composition 11-D prescribed to the individual (11), the dosage 11-P (which can include the time of dosage administration) and the other identifiers 11-I to the data of the database 18. Namely, the database 18 comprises predetermined knowledge of the symptoms 18-$s$ of the condition 18-C and the side effects 18-E of the therapeutic composition 18-D as well as a clinical average of the posology 18-P therefor. The controller 14 thus makes an initial comparison 13 of 11-C to 18-C, of 11-S to 18-S, of 11-D to 18-D, of 11-E to 18-E, of 11-P to 18-P.

The data of the database 18 is modulated by machine learning. A plurality of individuals 111 (see FIG. 1) have provided and continue to provide feedback 111-F along with their identifiers 111-F. The controller seeks to identify similarities between 11-F and 111-F and similarities between 11-I and 111-F for a common therapeutic composition (11-D⇔40 18-D) treating a common condition (11-C⇔18-C) in order to identify the optimal posology range in which the individual 11-F confirms an absence of symptoms (11-S) and side effects (11-E).

In an embodiment, as shown in FIG. 1, the system 10 includes the physician interface 22 as mentioned above as well as a monitor interface 24 in communication with the controller 14. The monitor can be an additional health care professional, a care giver, a parent, or any other type of supervisor and/or monitor as can be contemplated within the context of the present disclosure. As such, the monitor can receive the real-time feedback inputs of the individual user and/or the prompted questions from the controller 14 to the individual 11. When the individual is a child, the monitor ca be a parent and batter assess the prompted questions 14-Q of the controller 14 for providing more articulate input 11-F by the monitor to the controller 14. Moreover, the monitor can receive reports based on the individual's feedback (11-F) similarity to the aggregate feedback 111-F. In another embodiment, the physician enters the individual's general initial identifies via the physician interface 22. In another embodiment, the individual's monitor provides the initial identifier via the monitor interface 24.

The memory 18 comprises a plurality of computer-Implemented processes for the above iterations based on known statistical algorithms, computational statistics, machine learning and algorithms therefor, pattern recognition, bioinformatics, biostatistics, data mining, iterative methods in statistical estimation, clustering or cluster analysis and the like as is known in the art.

In an embodiment, the memory 16 uses the foregoing algorithms in Implementing the protocol generally exemplified below.

Computer1 Implemented Protocol Chart of System 10 and Components Thereof

System (10) Comprises:
A controller (14)
A user interface (12) for the individual (11) to provide data input (11-F including 11-I)
A physician interface (22)
A monitor interface (24)
A database 18 comprising a user updated databank for receiving information from a plurality of users (111) including individuals (11), physicians and monitors, thereby comprising a plurality of feedback 111-F including an aggregate of identifiers 111-I from the plurality of users 111
A dose calculator (20) that can form part of the database (18) or be one in the same with database (18)

Database (18) Comprises:
List of medical or mental health conditions (18-C)
List of therapeutic compositions (18-D) for treating respective conditions (18-C)
List of symptoms (18-S) including incremental degrees thereof related to a respective condition (18-C)
List of side effects (18-E) including incremental degrees thereof related to therapeutic compositions (18-D)
The known clinical average posology (18-P) for a therapeutic composition (18-D) in treating a respective condition (18-C)

Data Input (11-F)
Individual's medical or mental health condition (11-C)
Therapeutic composition (11-D) to treat the condition (11-C)
Prescribed posology (11-P)
Individual's identifiers (11-I) including real time health conditions independent of 11-C Comparison (13) Between Individual Data Input (11-F/11-I) and Database Knowledge
Controller (14) compares (13) data input to information of database (18), including:
Matching 11-C to the corresponding 18-C (denoted herein as M1)
Matching 11-D to the corresponding 18-D (denoted herein as M2)
Identifying symptoms related to 11-C=18-S related to 18-C (denoted herein as M1-S)
identifying side effects related to 11-D=18-E related to 18-D (denoted herein as M2-E)
Comparing (13) 11-P to 1B-P for the same therapeutic composition (11-D=18-D) in the treatment of the same condition (11-C=18-C) and identifying discrepancies therebetween.

User Feedback (11-F)
The controller (14) prompts the individual (11) to provide feedback (11-F) with symptom specific inquiries (14-Q) in view of the identified symptoms (M1-S) and with side effect specific inquiries (14-Q) in view of the identified side effects (M2-E).
Prompting (14-Q) is schedule-specific i.e. it occurs at predetermined times based on M1, M2, M1-S, M2-2 11-F (Including 11-I)
Controller (14) prompts (14-Q) the individual (11) to respond to:
the presence or absence of identified symptoms (M1-S) or identified side effects (M2-E)
the time of day that M1-S or M2-E occurred
the type or particularities of M1-S or M2-E
the severity of M1-S or M2-E User-Updated Databank
a) A real-time updated bank (18-B) of feedback (111-F including 111-I) from a plurality of users (111) regarding 18-S, 18-E and 18-P
b) A real-time updated bank (18-B) of users (111) having respective identifiers (111-I)

Modulation of Data—Machine Learning
The controller (14) clusters the feedback (111-F) of the User-Updated Databank (18-B) based on predetermined commonalities and updates the Database (18) thereby readjusting in real-time 18-S related to a particular condition 18-C, as well side effect 18-E and posology 18-P related to a particular therapeutic composition 18-D for treating that particular condition 18-C
The controller (14) compares (13) the individual's data input/feedback (11-F) to the readjusted information of the Database (18) by way of the foregoing Comparison Between individual Data input and Database Knowledge
The controller (14) clusters users (111) in the User-Updated Databank (18-B) having common identifiers (111-I) based on the identifiers (11-I) of the individual (11), thereby matching the individual (11) with one or more clustered categories of users 111 based on commonalities between 11-I and 111-I
The controller (14) identifies (13) the clusters of common feedback (111-F) related one or more clustered identifier categories (111-I) matching the individual's identifiers (11-I)
The controller (14) compares (13) the feedback (11-F) of the individual (11) obtained in a linear manner to the clusters of common feedback (111-F) related to one or more clustered categories (111-F)
The controller (14) determines (13) the greatest similarity of the individual's feedback (11-F) obtained over several iterations to the clusters of common feedback (111-F) related to one or more clustered categories (111-I) having the greatest similarity to the individual's identifiers (11-I)

Iterations
The controller (14) seeks to narrow the posology range 18-P based on at least two parameters:
to the smallest range containing the probable optimal posology for a given individual;
the above range being of a length that provides for a titration program that does not exceed a predetermined preferred number of days
The controller (14) implements several iterations of data input (11-F) from the Individual (11) and of comparisons (13) thereof to the modulated or adjusted data of the database (18), returning with new inquiries (14-Q) for the individual (11) for still further data input (11-F) for still further comparisons (13) until a satisfactory posology range is obtained based on the at least two parameters Results
Based on the iteration above, the controller (14) provides a posology range on the basis of an individual's similarity to the aforementioned clusters and the predetermined parameters
The individual's posology 11-P is readjusted and a new suggested posology 11-P' is provided comprising a probable optimal posology Titration Program
Based on the above RESULTS, the physician sets up a titration program (11-T) for the individual
The physician communicates the titration program to the Controller (14)

Titration Program Monitoring—Further iteration

The controller (14) monitors the titration program (11-T)

A The controller prompts (14-Q) user feedback (11-F) during the titration program (11-T)

A The controller 14 implements further iterations including inquiries (14-Q) and comparisons (13) as described above in order to identify (13) the optimal posology within 11-P'

Reports and Databank Update

The controller (14) provides a report to the physician via the physician interface (22)

The physician confirms the optimal posology based on the result, iteration and comparison reports The physician communicates their confirmation to the controller (14)

The controller (14) updates the databank (18-B) in real time regarding the individual's identifiers (11-I), the individual's feedback (11-F), the suggested posology (11-P'), the titration program (11-T), the titration program related user feedback (11-F), the computer obtained optimal posology within 11-P', the physician-confirmed optimal posology The present system therefore provides of monitoring and identifying posology efficacy. Moreover, the present system provides for monitoring and identifying side effect severity. Furthermore, the prese system provides for monitoring and identifying symptom severity.

General Description of Non-Limiting Practical Example (System 100)

System 100 comprises an application (i.e. application software for the computer implementable steps, also known as app) that visually communicates with the users via the interface.

Figure 3:
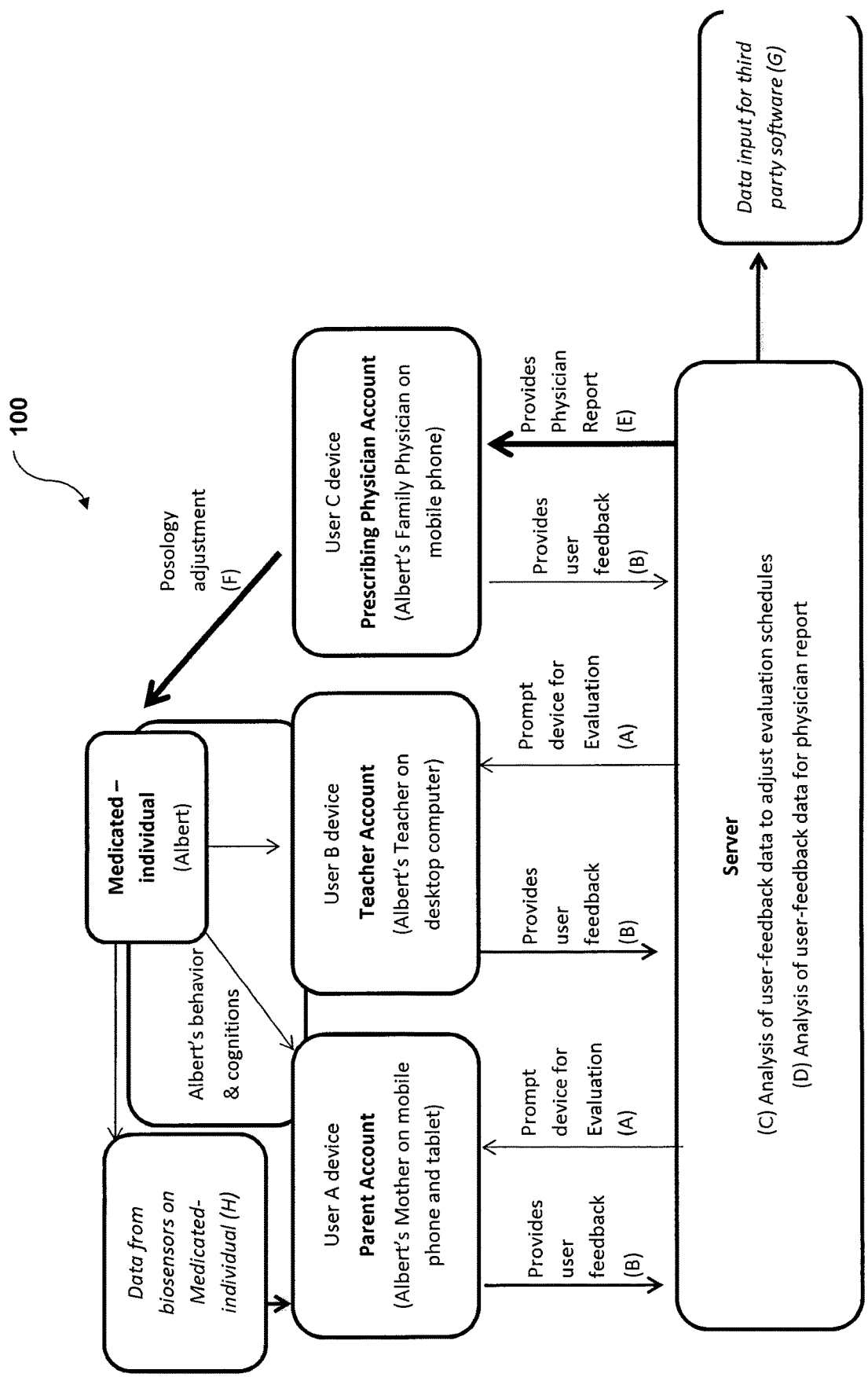
FIG. 3 is a schematic representation of user interaction with a system for monitoring and identifying posology efficacy for an individual in accordance with a non-restrictive illustrative embodiment of the present disclosure.

As demonstrated by FIG. 3, the application of system 100 prompts (arrows A) three users to make an evaluation via respective user interfaces 12 (User A Device, User B Device and User C Device) with regards to the medicated-individual Albert. The users in this case are Albert's Mother who communicates with the server (comprising both a controller 14 and a database 18) via User A Device, Albert's teacher who communicates with the server via User B Device and Albert's prescribing physician who communicates with the server via User C Device. These three users evaluate Albert in accordance with the prompted questions (arrows A) and provide their user-feedback (arrows B) back into the server. The system 100 analyses the accumulated user-feedback from all users in order to adjust the evaluation deployment schedules of the users to better measure the strengths and weaknesses of the current posology (C). When the prescribing physician makes the request, the server, analyses the accumulated user-feedback from all users (D) in order to generate a physician report to assist the physician in adjusting the posology for optimal effect (E), A new prescription is made (F), and users are prompted make evaluations with regard to this new posology (A). The same data that was used in the physician's report can be inputted in third party software (G). Data taken from a biosensor device (heart rate and movement data) is Inputted via the parent's device into the server database (H).

Evaluations

In an embodiment, the system 100 prompts the users to make evaluations concerning the medicated-individual. The nature of the evaluations and their deployment schedules are specific to the account type (e.g., parent and teachers have different evaluation objectives and schedules). The evaluations are all preformed on the user-device (interface), and consist of questionnaires, computerised tests (e.g., neuro-cognitive evaluations) any other means of collecting data that pertains to the efficiency or negative effects of the medication, and to the state of the condition for which medication is being prescribed.

Of course, as discussed for system 10, it is possible for the target individual make self-evaluations.

Evaluation Prompts

The application of the system 100 sends reminders (email and in-device prompts such as push-notification and pop-ups) to initialize or complete specific evaluations that are past due date.

Biosensor Feedback

Measures such as heart rate, respiration and skin conductance, derived from wearable technology and other sensor-based technologies, send data into the target individual's device that is in turn sent to the server for analysis. For example, heart rate and movement data from a wearable biosensor watch provides pertinent data concerning the side effects and efficiency of ADHD medication.

Analysis of Data

Data collected from these evaluations (i.e., user-feedback) are sent to the sewer. The data is analyzed along with the data from other users concerning the same target individual; these analysis may modify the evaluation schedules of the users (e.g., reports of insomnia in a symptom questionnaire for ADHD medication will prompt a daily sleeping evaluation questionnaire for parent accounts, and will add a sleepiness scale on the evaluations of teacher accounts).

Physician Report

When prompted by the prescribing physician, the collected data is analyzed and presented in a report form on the prescribing physician's user-device. The application selects, synthesizes, summarizes and produces statistical analyses with the data collected from user-feedback; this information is presented in a concise manner by means of tables, and graphical representations such as bar graphs, line graphs and pie charts, to assist the prescribing physician in providing an optimal posology to the medicated user. The report content and structure is customizable by the physician.

Titration System

The titration system in accordance with a non-limiting example provided herein allows to test the effects of several different posologies on an individual. Individual differences that are difficult or expensive to predict (e.g., variation in brain architecture) cannot be accounted for when prescribing a drug. The titration system addresses this issue by allowing users and a prescribing doctor to examine the effects of several different posologies during a period of several weeks. Because neither the parents nor the doctor knows which of the four weeks (or examples, (of course any number of weeks can be provided) are associated with the four different posologies, for example, (i.e., double blind procedure) (of course any number of posologies can be provided) an objective evaluation of the best posology is possible. The system 100 allows for pertinent data (feedback) to be collected by the target user (and other users) and strategically displayed to better evaluate which of the posologies are best for them.

The objective of the titration system to examine the effects of several different posologies, on a target individual, so that they may be compared in a systematic end objective manner. The titration system uses the features described above to prompt evaluations, generate user-feedback data and physician reports in order to objectively select which of several posologies is optimal for the target individual. Essentially, this system allows, a prescribing physician to conduct a double-blind clinical experiment on a single user (see FIG. 5).

Figure 5:
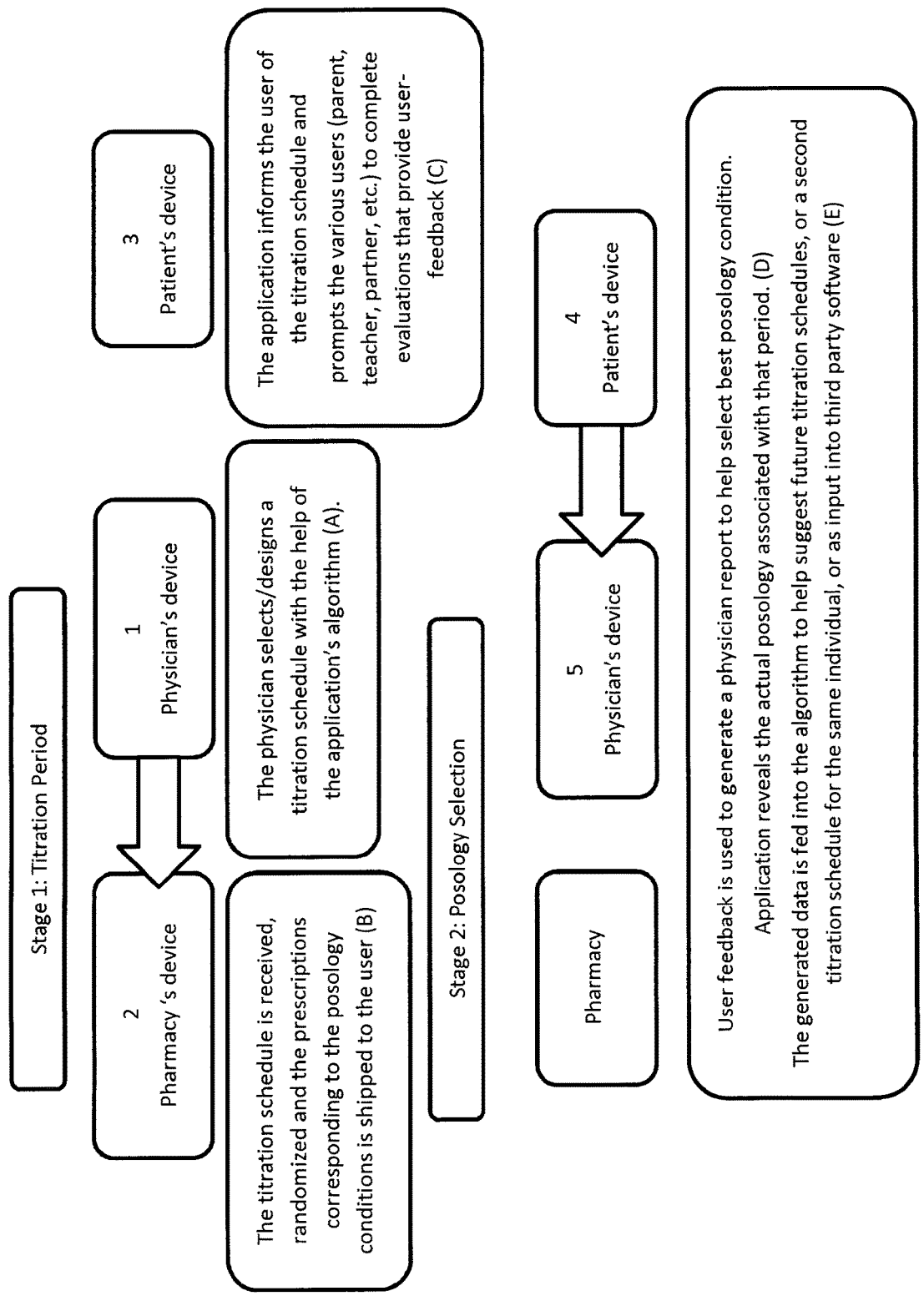
FIG. 5 is a schematic representation of a titration system provided by the system and/or method for identifying posology efficacy for an individual in accordance with a non-restrictive illustrative embodiment of the present disclosure.

FIG. 5 shows the titration system including two stages: Stage 1: the Titration Period and Stage 2: the Posology Period.

While the physician decides the posologies that will be tested and compared (i.e., posology conditions), the system 100 handles the randomizing, scheduling and interaction with a participating pharmacy for example. As such, the present system's titration module makes it possible, and very simple, to run a personalized double blind clinical trial.

The titration system or process in FIG. 5 is as follows:

The physician has an interface or user's device 1 and the target user has a patient's device. As such, both the physician and the target user have the system's application and their accounts are linked (see above), The target user's address is entered and stored.

(Step A): The physician selects and designs a titration schedule with the help of the system's algorithms.

Figure 4:
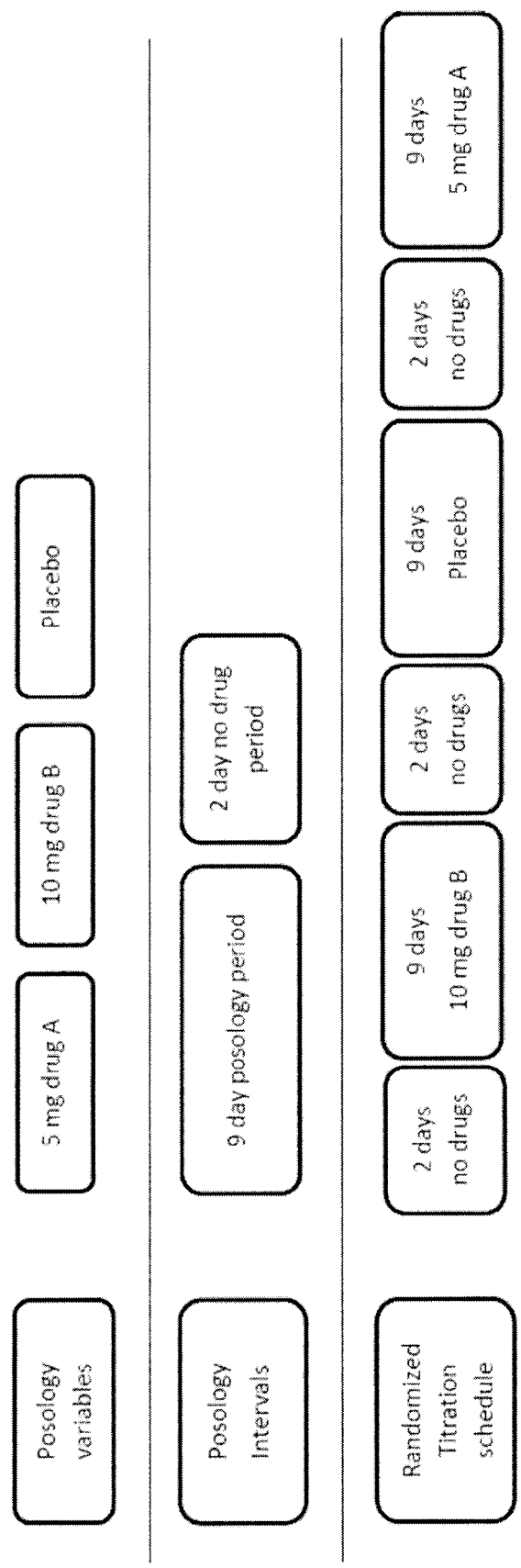
FIG. 4 is a schematic representation of how posology variables and the posology intervals comprise the final randomised titration schedule provided by the system and/or method for identifying posology efficacy for an individual in accordance with a non-restrictive illustrative embodiment of the present disclosure.

More specifically and as shown in FIG. 4, the physician (or person prescribing the medication) uses the system's application to characterize the posology conditions that will be compared:

P1) posology variables, i.e., what vary from different posology conditions, e.g., the type of drug and dosages.

P2) posology constants, i.e., what remains the same between posology conditions, e.g., the time of day and frequency of drug intake, directions such as taking the drug on an empty stomach.

P3) posology interval: the amount of time each posology condition will last, and if there is a period of time in-between conditions when no drugs are taken ("flush-out period").

The result of P1, P2 and P3 is a titration schedule. An example of a titration schedule is:

P1—Three posology conditions, which differ in terms of dose and drug type: 5 mg of Drug A, 10 mg of drug B & placebo (posology variables).

P2—AU three posology conditions are taken once per day, in the morning, on an empty stomach (posology constants).

P3—Each posology condition will be taken for 9 days, with 2 days with no medication in between each 9 day period (posology interval).

FIG. 4 illustrates how the posology variables and the posology intervals comprise the final randomized titration schedule.

By selecting the maximum dose and the type of medication, the system's algorithm suggests a number of ranked titration schedules based on the outcome of previous titration schedules.

The physician then decides what data the target user should to collect via their application (e.g., depression questionnaire once per day in the evening). The system may suggest a number of questionnaires or other data collection methods depending on the medication that comprises the titration schedule. The target user can have other users collect similar data (have their partner fill out a daily mood questionnaire with regards to the target user).

Once the titration schedule is set within the system's application (Step B in FIG. 5), a prescription is printed via the application, signed by the prescribing physician, or signed directly in the application via an electronic signature. The prescription is sent (via scan, picture or fax, or directly via an electronic signature) to the pharmacy partner, which has access to the system. The actual order of the posologies is randomized and known only by the pharmacist(s) via their pharmacy account privileges (for example, 1st nine day period, I, is 10 mg; the 2nd nine day period, II, is 5 mg; and the final nine day period, III, is placebo—this information in unknown to the user or the physician).

A titration schedule that has been randomized is called a randomized titration schedule. The posologies are mailed by the participating pharmacy or online pharmacy partner according to the randomized titration schedule. Drug bottles are clearly marked I, II, III, and the doses it may contain.

Therefore, the titration schedule is received, randomized and the prescriptions corresponding to the posology conditions is shipped to the target user. The target user's interface device 3 clearly indicates from which bottle to take the medication from on a given day and other details pertaining to the randomized titration schedule-all the while keeping the actual posologies variables secret (e.g., the actual type and dosage of each condition).

In step C, the system's application informs the user of the titration schedule and prompts the various users (parent, teacher, partner etc.) to complete evaluations that provide user-feedback. Therefore, during the titration period, the user(s) is (are) prompted to make evaluations and send user-feedback via the application, as described above. For example, each day during the titration schedule the system's application sends reminders and prompts to the users to make behavioral and side effect evaluations (using the feedback module).

In step D, after the titration period is ended, the parents meet with the doctor, and the system's application generates graphs illustrating differences between the posology conditions (using the feedback module). Together, they select the posology conditions. The physician may prompt a titration physician report, i.e., specific set of graphs based on the data collected via the feedback module, that compares the advantages and disadvantages of each posology period (I, II or III) to assist the physician (and the user) in selecting which of the posology conditions was the best for the target user. Once the best posology condition is selected (e.g., II), the physician can prompt the application to reveal its corresponding posology (e.g., II=5 mg of drug α). The physician makes a normal prescription with the selected dosage. The user can continue to use the same pharmacy partner used in the titration system; the pharmacy may thus acquire a new long-term customer.

In step E, the data generated during the titration period is fed into the algorithm to improve its ability to suggest appropriate titration schedules for future users, to suggest another titration schedule with more precise doses with the same user, or as input into third party software.

In another embodiment, the titration program consists of providing a a base line with a target individual and utilizing a score or a biosensor. Then comparing the score or the result of the biosensor once the target individual has received the therapeutic composition.

Integration with Other Software

As shown in step G of FIG. 3, the system's application can be used in conjunction with third party software that uses an algorithm to select treatment or posology variables. Using the features described above (in particular evaluations, user-feedback and analysis) the application may provide data to inform the software's algorithm with real-life data to help determine the best course of treatment action.

Communication System

The communication system serves as a communication platform where the users exchange information, data, documents, messages and information in an effort to coordinate the management or a medical or mental health condition, including drug withdrawal.

The communication system described below has elements that are similar to the posology system described above. While the posology system is specific to finding an ideal posology, the communication system deals with all aspects of treatment and management of the condition, which may or may not include medication.

Accounts

The communication system is intended to help the target individual (i.e., the person that is the object of the medical or mental health intervention who may be medicated or not), relatives, healthcare professionals, social works, lawyers, teachers and others work together; because these individuals have different objectives and needs, the application has specific account types. For example, a target individual account displays information and functionalities that is relevant to the target individual, while a physician account provides those pertinent to a health care professional. It is the target individual account that controls what information is available to other accounts, via establishing permissions. Other accounts include relative, teacher, social worker, legal and psychologist accounts. If the target individual is a minor, its legal guardian has control over the target individual account via a parent account.

Figure 6:
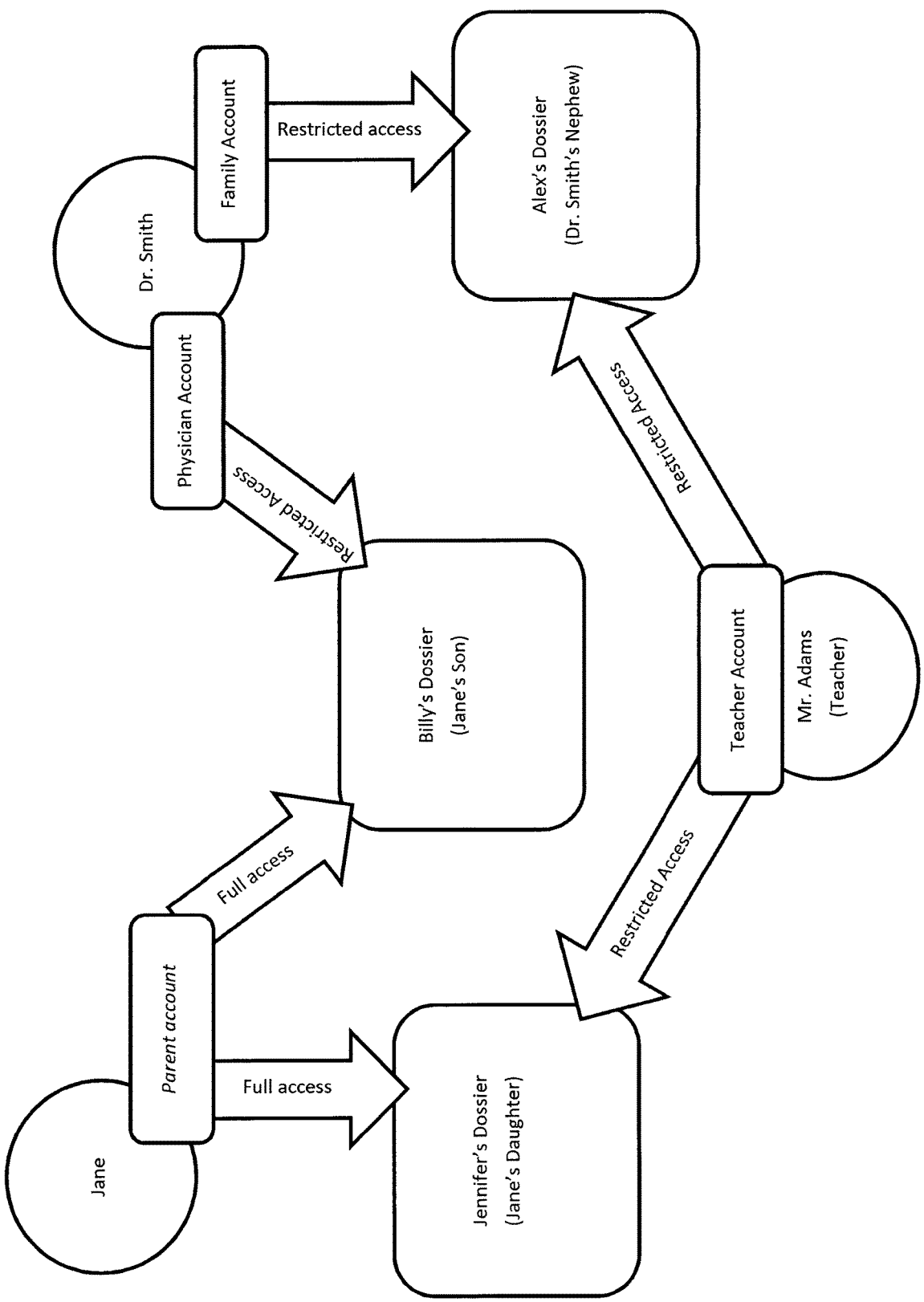
FIG. 6 is a schematic representation of communication relationships between users, accounts and dossiers of the system and/or method for identifying posology efficacy for an individual in accordance with a non-restrictive illustrative embodiment of the present disclosure.

For example, FIG. 6 illustrates that accounts are associated with a single individual, Billy, who is diagnosed with a condition, C-Billy for example, across several devices. These devices include interfaces that are in communication with the controller of the system 10 or 100 and provide account platforms thereon to the different users. For example, Jane is Billy's mother and she has a parent account that has full access to Billy's dossier. Jane also has a daughter Jennifer, who is diagnosed with a condition C-Jennifer. Jane has full access to Jennifer's dossier t via Jane's parent account. Jane can access her account via from her mobile and her laptop for example. Mr. Adams is a teaches and he has restricted access to Jennifer's dossier as well as to Alex's dossier. As Billy's physician, Dr. Smith, has restricted access to Billy's dossier via his physician account but as Alex's uncle, Dr. Smith also has access to Alex's dossier via a family account. A dossier is data is contained within the controller's database (i.e. the server). A dossier comprises the data associated with a target individual (e.g., Jane manages her son Billy's dossier via her parent account; Dr. Smith manages Billy's dossier via her physician's account). It is possible for an individual to have both a parent and a physician's account (e.g., Dr. Smith's nephew was diagnosed with a condition C-Alex; her nephew is her relative and not her patient, thus she is linked to her nephew's account via a relative (or family) account); at any time, the user can switch between accounts via a Change Account function.

An account can be associated with one or more dossiers (a parent may have several children; a physician typically has many patients. FIG. 6 illustrates non-limiting examples of the relationship between individuals, accounts and dossiers).

In an embodiment, the application's functionalities are dossier-specific: before using the application, the target individual in question must be selected, via the target individual select screen. Every time the application is started, the target individual select screen appears. The target individual select screen is available at any time to switch between dossiers.

In an embodiment, the target individual has special privileges: namely, the right to determine limits and permissions of other accounts associated with the dossier. Moreover, all account links (see below) between a dossier and other accounts must be approved by the target individual account (e.g., Jane received a relative link request from her neighbor, which she refused).

An account link is a set of permissions that allow an outside account to have specific access, and to make specific changes, to a dossier, specified by both the user of the target individual account and what type of account is being linked (e.g., physician, relative).

For example, Jane allowed Dr. Smith to link her physician's account to her son Billy's dossier, giving Dr. Smith full access to medical and symptom-related Information. The parent account holder can modify permissions at any time.

The Linking Process

In an embodiment. In order to establish a link between two accounts: —The user can locate an account using the account search function: Name, Address, Account Type (relative, physician etc.). If the individual that is being searched for (e.g., Dr. Smith) has the appropriate account in the database (e.g., Dr. Smith has a physician account), then the individual being searched for gets a confirmation notification in their account module and a message in their notification area (explained below). The individual that was located for must then confirm the nature of the relationship (e.g., Dr. Smith must confirm, or deny, that Billy is her patient). Upon confirmation, the accounts are now linked. If an account already exists for the individual, missing information is updated (Dr. Smith's office hours). The user can now click on the account icon in the account module set permissions and modify information with regards to this individual.

If the individual is not found by the account search function, the user can choose to send an automated email asking the individual to download the application and create an account. An unlinked account representing the individual can be created, and information (e.g., address) can be entered by the user. Each account type corresponds to a specific interface and default restrictions, some of which way be modified by a parent account.

General Interface

Figure 10:
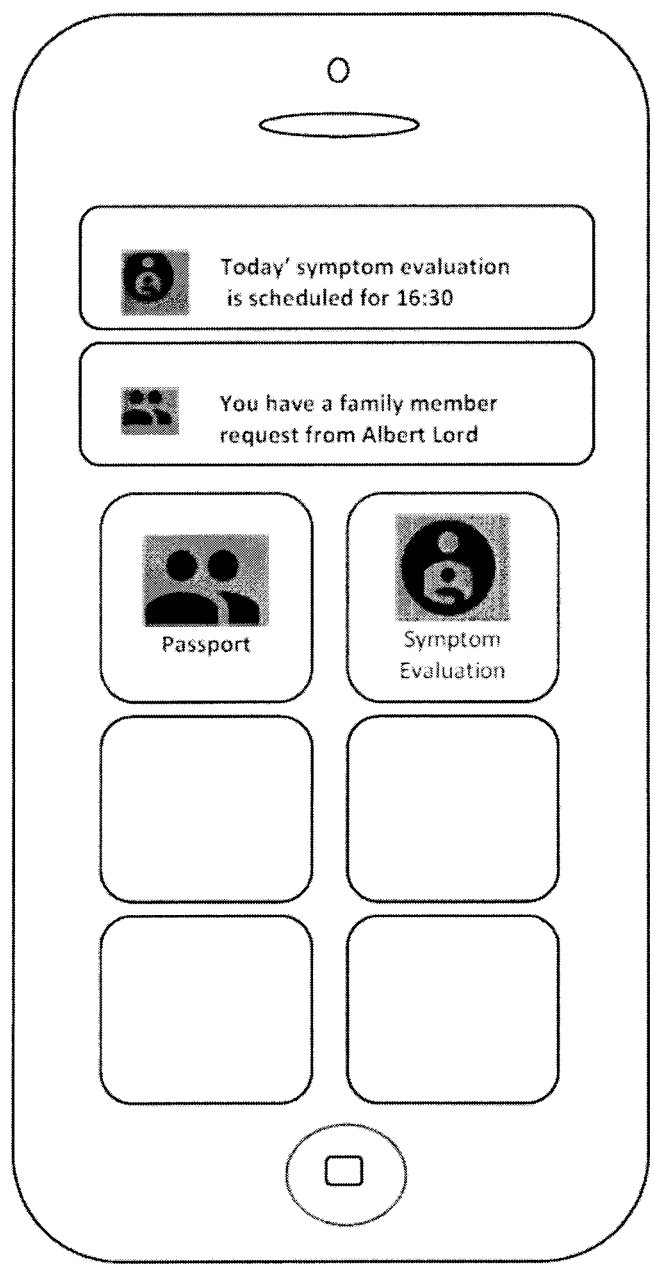
FIG. 10 is an illustration of a user interface of the system for monitoring and identifying posology efficacy for an individual in accordance with a non-restrictive Illustrative embodiment of the present disclosure.

In an embodiment, the Welcome Screen (see FIG. 10) has an icon for each active module (Module icons). Clicking on the icon brings up the module's main screen (e.g., the account icon leads to the main account screen). Closing the module page brings back the Welcome Screen (by pressing the home icon).

At the top is the Notification Area, a space dedicated to text messages (welcome message, reminders, alerts, etc.). If more than one message is required, the Module Icons are pushed down to make space. Messages can be clicked to open the relevant module (a small icon representing the relevant module appears on the message to help the user build a cognitive map of the application's architecture).

Module icons are dynamic (in their location and through time). Most Module Icons are permanent, while others are time sensitive, e.g., for certain functions that are important to perform (e.g., connect with your physician). Module Icons can appear at specific times (at first, a minimal amount of Module Icons appear to minimize cognitive overload).

Each module is assigned a rank (by the application designers) that will determine its location within the Welcome Screen. User-initiated customization options may be made available in later versions.

Account Module

In en embodiment, the account module manages accounts and the linked process between different accounts, notably:—search for individuals using the account search function; —send contact messages offering to link accounts; —send premade email offering to download the application; —create/delete/edit account details; —If the accounts are linked, establish permissions.

Feedback Module

In an embodiment, the Feedback is similar in principle to evaluations found in the posology system, but of a much wider scope. This section permits the user to collect data (typically behavioral and cognitive) concerning the target individual from a wide range of evaluation types. In addition, the presence of interfering life events (emotionally disturbing events, illness, etc.) is documented and a score is attributed to its perceived impact. The nature of the evaluations and their deployment schedules are specific to the account type (e.g., psychologists and teachers have different evaluation objectives and schedules) and the condition of the target individual (e.g., depression and alcoholism require vastly different types of feedback).

The type and frequency of the requested feedback is dynamic and changes as more data is collected and analyzed by the application of system 100. Certain types of data trigger changes in the frequency and nature of the requested feedback. Also, some users may request specific feedback from other users (e.g., a teacher may request that a parent take a weekly "emotional event questionnaire").

Most types of feedback evaluations are optional and schedulable (e.g., if the parents accept the teacher's proposal, they can schedule the "emotional event questionnaire" to each Friday, with the help of the application's calendar function). The application will prompt the user to initiate or complete the questionnaire (e.g., each Friday a notification appears on the parent's interface device reminding them that the evaluation is scheduled for today), and continues to send reminders if they fall to complete the evaluation in time.

The evaluations are all preformed on the user-device, and consist of questionnaires, computerized tests (e.g., neurocognitive evaluations) any other means of collecting data that pertains to the efficiency or negative effects of the medication, end to the state of the condition for which medication is being prescribed. It is possible for the target individual make self-evaluations.

Some Tests Include:

Medication/Prescription Module:—finked to the posology system, indicating the posology to the users as determined by the system; Create/delete/edit information relating to the prescription.

Questionnaires:—Questionnaires relating to the target-individual's medical or mental health condition are presented.

Medical measurements:—create/delete/edit information relating to medical measurements: height, weight, blood pressure and heart rate; —enables to place a child's measurement within a height and weight graph (usual growth cuives).

Digitalized neurocognitive and psychological tests:—to be done directly on the device (for example, digitalized version of a working memory test, sustained attention tests, etc.)

Open ended questions: —Audio recordings or text based-form can be used to answer open ended questions (e.g., how do you feel today?).

Biosensor feedback:—Biosensor-based devices, such as wearables, can send heart rate, respiration and skin conductance data (and many other physiological measurements) into the target individual's device that is in turn sent to the server for analysis (for example, heart rate, blood pressure and respiration data taken from a wearable biosensor watch will provide pertinent data for someone with an anxiety disorder).

Feedback Prompts

As the posology system described above, the system's application sends reminders (email and in-device prompts such as push-notification and pop-ups) to initialize or complete specific feedback-related activities that are past due date. These feedback-prompts are associated with a calendar within the system's application, or synced with a third-party calendar (e.g., Google calendar).

Analysis of Data

Data analyses operate on the same principles as the posology system, but treat a much wider range of data (e.g., includes medical measurements), and potentially for a much longer time period (years end decades). Data collected from feedback-related activities are sent to the server. The data is analysed by an algorithm along with the data from other users concerning the same target individual. These analyses may modify the feedback schedules of the users, i.e., the type and frequency of feedback that is required by the application (via feedback prompts) for each user. Feedback schedules dependent on the condition and the user. For example, a psychologist may be asked by the application to fill out a specific evaluation during each visit from the target individual.

In an embodiment, the application's analysis of the feedback data also prompts messages or alerts to specific users. For example, FIGS. 7 and 8 depict user-application interactions in the communication system.

Figure 7:
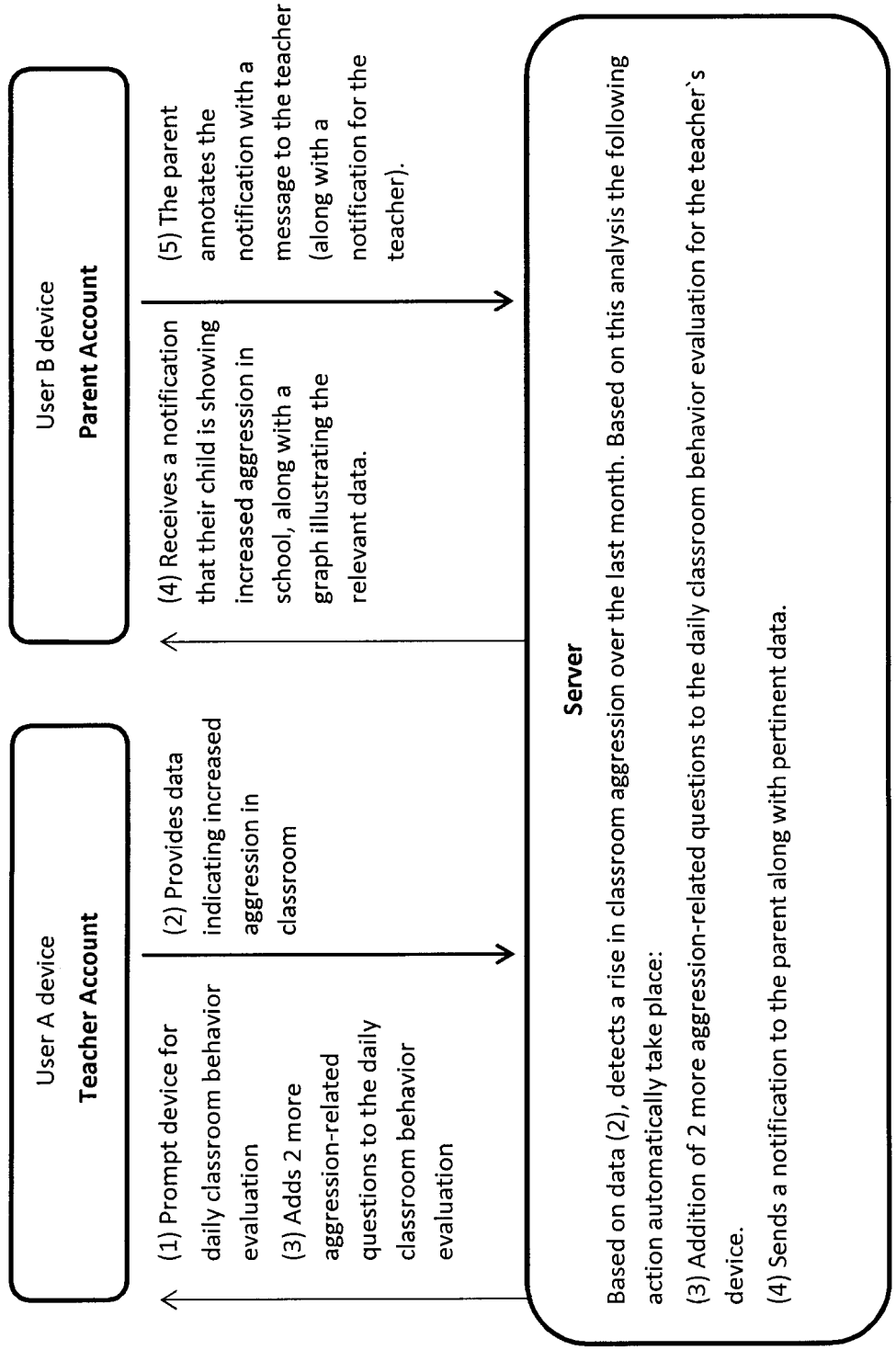
FIG. 7 is a schematic representation of user interactions in the communication system of the system for monitoring and identifying posology efficacy for an individual in accordance with a non-restrictive illustrative embodiment of the present disclosure.

In FIG. 7, a teacher via their User A Device interface accesses their account and is prompted (1) by the system for daily classroom behavior evaluation and in response provides data (2) indicating that a child is getting more aggressive at school (from data derived from a daily classroom behavior evaluation), both the linked parent (via their User B interface) and psychologist accounts are automatically notified (4) of this rise in aggression, along with a graph illustrating the trend. In this example, the parent and psychologists can then annotate the notification (5) and leave a comment via the notepad function. In addition, the application automatically adds two more aggression-related questions (3) to the daily classroom behavior evaluation to be completed by the teacher. To continue with this example, the psychologist requests that the parent account holder take a retrospective emotional stability questionnaire once a week; the parent accepts this request, and schedules this Friday at 3:00 PM.

Figure 8:
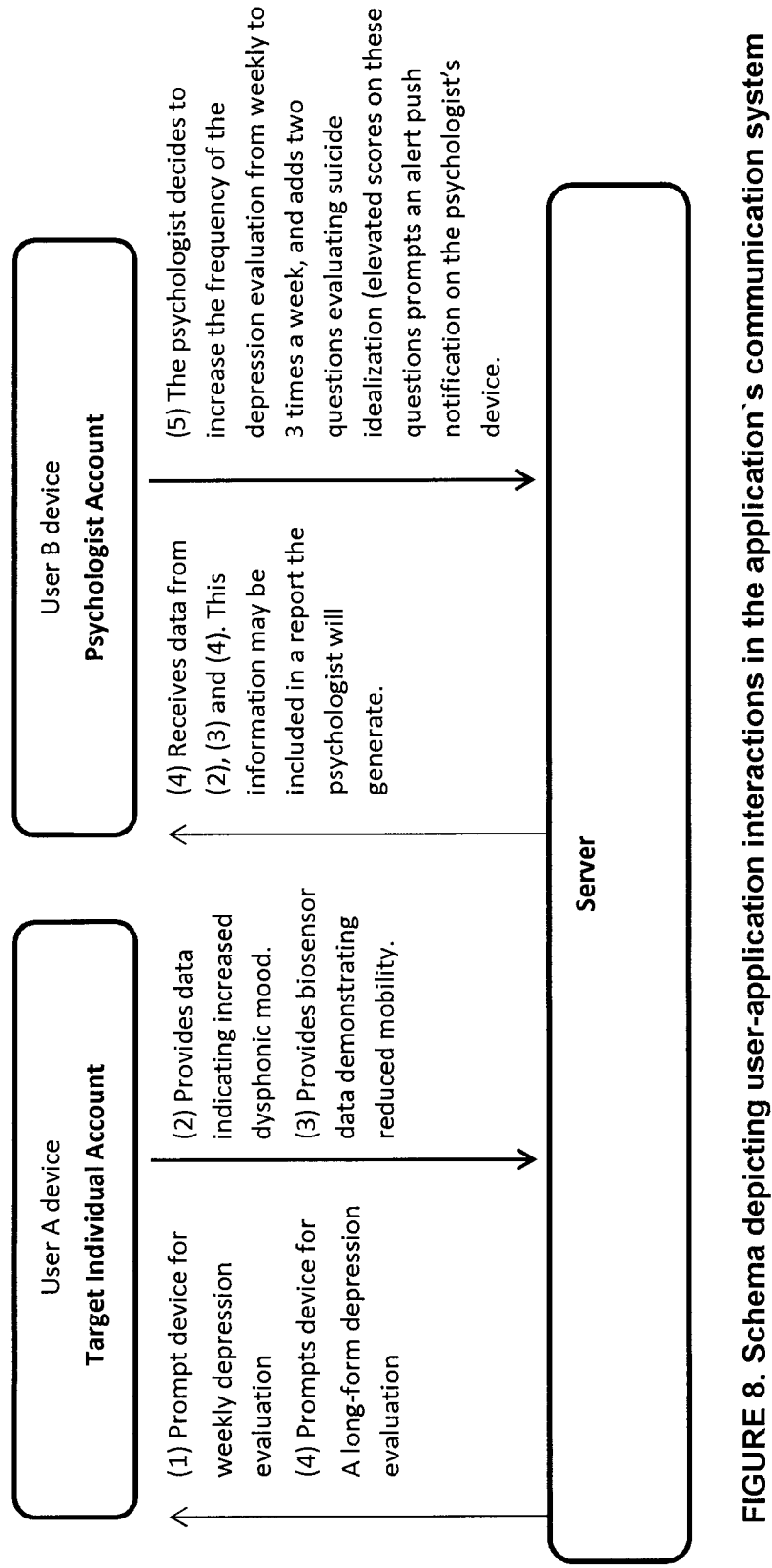
FIG. 8 is a schematic representation of user interactions in the communication system of the system for monitoring and identifying posology efficacy for an individual in accordance with a non-restrictive illustrative embodiment of the present disclosure.

In FIG. 8, a targeted individual is prompted (1) via their account accessed by their User A Device regarding their weekly depression evaluation. The targeted individual provides data (2) indicating increased dysphonic mood. The targeted individual also provides biosensor data (3) demonstrating reduced mobility. The Individual's psychologist received data from the individual's feedback to the server. This Information may be included in a report the psychologist will generate. The psychologist then provides via their User B Device to their account their assessment. In this example, the psychologist decides to increase the frequency of the depression evaluation frm weekly to 3 times a week, and adds two questions evaluating suicide idealization (elevated scored on these questions prompts an alert push notification on the psychologist's User B Device).

Generate Reports

Like the posology system, the reports present data in tables, bar graphs, line graphs and pie charts, but of a much wider range of formats and data choices. Many premade report types are specific to the account type and condition (e.g., a premade report specifically made for psychologists that are following a target individual that is diagnosed with depression).

Steps for generating reports include:—Select Predetermined Report Structures (e.g., side effect end symptom report for physician; monthly progress report for parents); —Select time scale (e.g., provides several options such as 7 days; 7 weeks; 7 months; custom time scales would be useful but perhaps in a later version.)

When prompted by the user, the collected data is analyzed and presented in a report form on the device. The application selects, synthesizes, summarizes end produces statistical analyses with the data collected from user evaluations; this information is presented in a concise manner by means of tables, end graphical representations such as bar graphs, line graphs and pie charts, depending on the type of report structure that is selected and its intended viewer. The report content and structure is customizable.

Progress reports for target individual's whose physician does not have an account: —These options are made available make a physician aware of the application. —The time scale of the report, and its form, may depend on the amount of data collected. —Email standard report to physician (enter email). —Email standard report to self (to allow to open and print report on a computer, to bring during visit). —Display standard report on screen, to show physician during visit.

Other application functionalities: —A calendar function (Integrated with the apple/Google calendar). —Standard reminders and alerts (push notifications). The system may send emails inviting different accounts (e.g., relatives) to download the application (if unlinked) or to complete questionnaires. Reminders are sent after a certain period of time, and for a limited duration. —A drop box to upload, download, delete, tag and flag a document (.doc, .docx, .pdf). Tags are simply key words that can be searched. Flags are tags that are specific to a level of importance. Other accounts can be tagged (that prompts a notification message in the other account's Notification Area). The ability to create folders to organize files would be useful, but can wait for a subsequent application version. —A notepad to write notes in a private manner or a message that is shared with a specific account(s).

Other Uses for the Application

The Use of the System for Withdrawal

The posology and communication systems can function in the context of drug withdrawal (over the counter, prescription, recreational and illegal drugs). In this manner, the posology system can adjust the drug withdrawal schedule (the timing of the diminishment of the dosage of a drug) in relation to the user feedback that is collected by the application, analyzed by the system and displayed to the prescribing physician. Similarly, the communication system assists the target individual and concerned actors in collecting and sharing data that will guide decisions impacting the drug withdrawal process.

The Use of the System for Clinical Studies

The posology end communication systems can equally function in the context of clinical or other research studies. On possibility is to use the titration system to establish optimal doses for a drug under study, such as recommended doses, maximum and minimum doses for the general public. This can be done in order to establish optimal doses for the general population and to determine optimal doses with relationship to a particular user variable, such as weight, age, sex, or a combination of variables. In particular, the system's ability to prompt user feedback via a mobile device allows the possibility to study the effects of a drug in the participant's everyday life with minimal intervention; because the feedback (questionnaire, neurocognitive testing, biosensor data, etc.) is collected in the participant's normal setting, the research profits from a high level of ecological validity.

Use of Other Data Types

The application also makes use of data that is taken from other means, such as diagnostic tests measuring an individual's genotype information, salivary analysis (e.g., levels of neurosteriods or specific proteins), blood sample analysis (e.g., levels of cortisol), EEG analysis (e.g., alpha to theta ratio in the frontal cortex) and the like.

Predicting Treatment Outcomes

Through assisted machine learning and data mining, the application reveals patterns and trends within the date that will be used to predict treatment outcomes and will serve as a basis for treatment recommendations, including posology-related recommendations for both the pharmacokinetic and titration modules.

Figure 9:
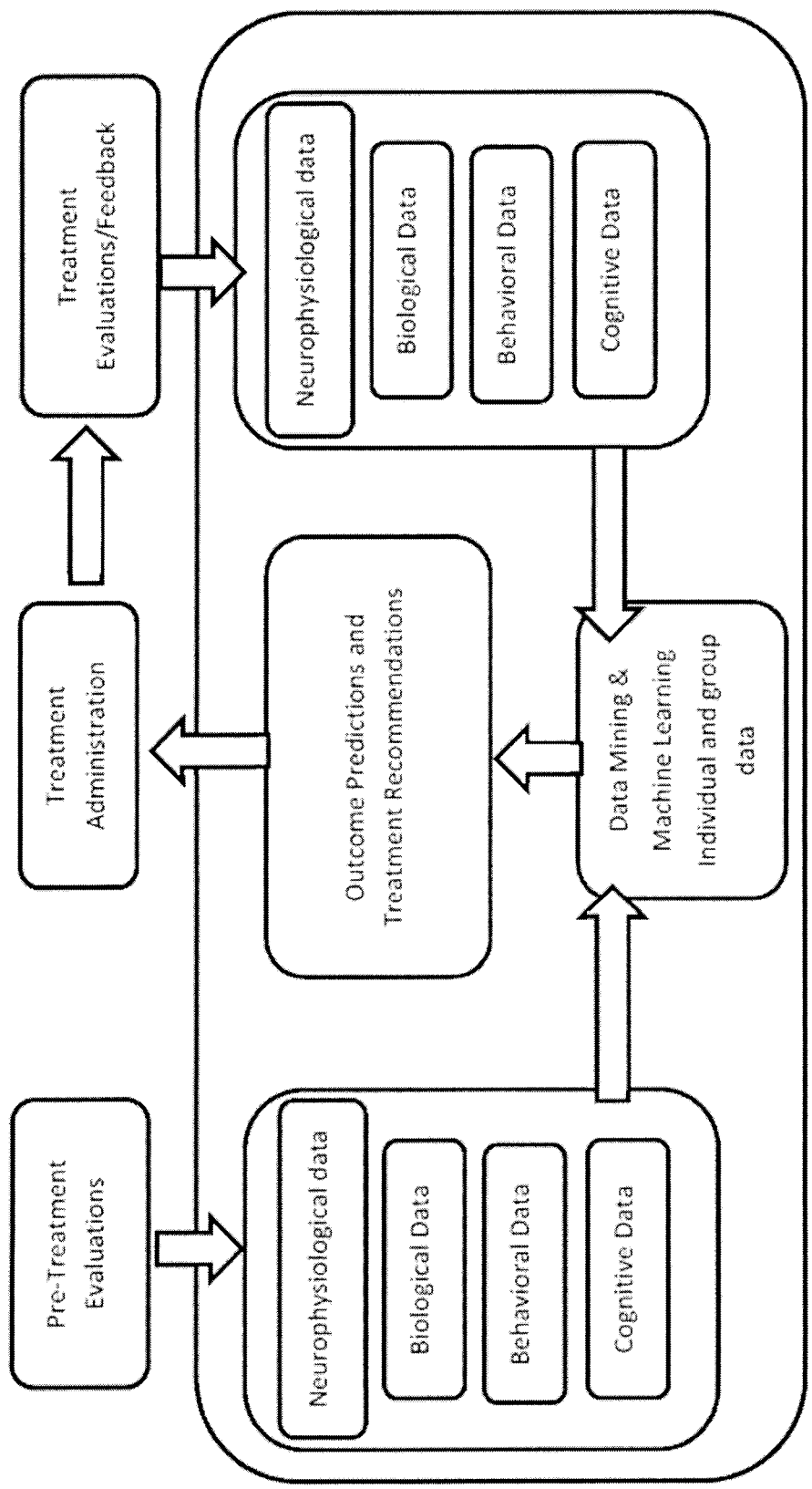
FIG. 9 is a schematic representation of the use of data provided by the system for monitoring and identifying posology efficacy for an individual to predict treatment outcomes in accordance with a non-restrictive illustrative embodiment of the present disclosure.

FIG. 9 exemplifies the use of data to predict treatment outcomes. A machine learning circuit is provided between pre-treatment evaluations and treatment evaluations/feedback. The pre-treatment evaluations include neurophysiological data, biological data, behavioral data, cognitive data. This information is then data mined along with real-time treatment evaluations and user feedback related to neurophysiological data, biological data, behavioral data, cognitive data. Therefore, data mining and machine learning is based on individual and group data fed from real-time treatment evaluations and pre-treatment evaluations and on that basis (as explained above for system 10) provides outcome predictions and treatment recommendations and thus provides a treatment administration which is refed back into the system for further date mining and machine learning.

In an embodiment, the user feedback described herein comprises behavioral symptoms.

In an embodiment, the present system and method and its various embodiments ca also be used in clinical studies for data collection of patients in order to assist in maximizing posology evaluation.

In an embodiment, the present system and method provide an educational tool for educating a patient with respect to their pharmacodynamics.

The various features described herein can be combined in a variety of ways within the context of the present disclosure so as to provide still other embodiments. As such, the embodiments are not mutually exclusive. Moreover, the embodiments discussed herein need not include all of the features and elements Illustrated and/or described and thus partial combinations of features can also be contemplated. Furthermore, embodiments with less features than those described can also be contemplated. It is to be understood that the present disclosure is not limited in its application to the details of construction and parts illustrated in the accompanying drawings and described hereinabove. The disclosure is capable of other embodiments and of being practiced in various ways. It is also to be understood that the phraseology or terminology used herein is for the purpose of description and not limitation. Hence, although the present disclosure has been provided hereinabove by way of non-restrictive Illustrative embodiments thereof, it can be modified, without departing from the scope, spirit and nature thereof and of the appended claims.

What is claimed is:

1. A computer implemented system for real-time, automatic and prompted interactive monitoring of a target individual having a health condition and having been assigned a therapeutic composition at an assigned dosage thereof for treatment of the health condition, the system providing for identifying the efficacy of posology for the target individual with respect to administration of the assigned therapeutic composition, the system providing for determining whether the assigned dosage should be modified in order to increase or decrease the dosage, the system comprising:

a remote controller comprising a processor and an associated memory of processor executable code that when executed by the processor cause the controller to execute computer implementable steps;

a user interface for a mobile handheld communications device, the user interface being in communication with the remote controller via a network and providing for receiving inputs from the user to be communicated to the remote controller and to communicate outputs from the remote controller to the user;

a database in communication with the remote controller and having stored thereon information related to a plurality of health conditions, a plurality of symptoms indicative of respective ones of the plurality of health conditions, a plurality of therapeutic compositions for treating respective ones of the plurality of health conditions, a plurality of side effects associated to respective ones of the plurality of the therapeutic compositions, and wherein the database further comprises:

a databank having stored thereon information related to a plurality of previous target individuals, wherein the information related to the plurality of previous target individuals comprises the health conditions and related symptoms of the plurality of previous target individuals, the therapeutic compositions assigned the plurality of previous target individuals in treatment of the health conditions of the plurality of previous target individuals, and the side effects of therapeutic compositions assigned to the plurality of previous target individual;

a dose calculator controller in communication with the database and comprising a processor and an associated memory of processor executable code that when executed by the processor causes the dose calculator controller to execute computer implementable steps:

receiving input via a dose calculator interface in communication therewith of clinical data regarding the posology of the plurality of therapeutic compositions for treating the respective ones of the plurality of health conditions;

calculating clinical averages of the input received via the dose calculator interface, wherein the clinical averages consider the dose range and the temporal range of administration of the therapeutic composition thereby providing a dosage-temporal average;

communicating the dosage-temporal average to the database for storage thereon;

wherein execution of the processor executable code stored in the memory of the remote controller causes the remote controller to execute the computer implementable steps of:

automatically storing on the database the dosage-temporal average information communicated to the database;

automatically storing in the databank in real-time the information related to the plurality of previous target individuals;

automatically statistically modifying the plurality of symptoms in the database and the plurality of side effects in the database in accordance with the information related to the plurality of the previous target individuals;

receiving information from the user interface via user inputs regarding the target individual's health condition and automatically comparing this information to the database to match this information to at least one of the plurality of health conditions in the database thereby automatically providing a matched condition and identifying one or more of the plurality of the statistically modified symptoms in the database indicative of the matched condition thereby providing identified symptoms;

receiving information from the user interface via user inputs regarding the therapeutic composition assigned to the target individual, automatically comparing this information to the database to match this information to at least one of the plurality of therapeutic compositions in the database thereby automatically providing a matched therapeutic composition, and automatically identifying one or more of the plurality of the statistically modified side effects in the database associated with the matched therapeutic composition thereby automatically providing identified side effects;

automatically prompting the user via the user interface by way of a visual and/or audial cues to provide real-time user feedback regarding the possibility of the target individual manifesting the identified symptoms or the identified side effects within predetermined parameters stored within the memory of the controller, wherein prompting within predetermined parameters comprises:

providing pre-determined questions stored in the memory of the remote controller to the user in real-time via the user interface related to the identified symptoms or the identified side effects;

schedule specific prompting at predetermined times of the prompting based on the probable occurrences of the identified symptoms or identified side effects wherein the schedule specificity and the predetermined times based on the probable occurrences of the identified symptoms or identified side effects are stored in the memory of the remote controller;

prompting in real-time the individual to respond to the presence or absence of identified symptoms and identified side effects including the time of day thereof, the type thereof, the particularity thereof, the severity thereof;

continuously prompting the user for feedback until the feedback is received;

receiving the feedback from the user in real-time by way of inputs via the user interface;

automatically determining in real-time based on the user feedback whether the therapeutic composition assigned to the target individual is administered at a dosage that should be modified by automatically executing the following computer implementable steps:

i. automatically comparing the assigned dosage over a period of predetermined time to the dosage-temporal average of the assigned therapeutic composition, wherein the predetermined time is stored within the memory of the controller;

ii. automatically identifying a discrepancy between the assigned therapeutic composition over the period of predetermined time and the dosage-temporal average for the assigned therapeutic composition;

iii. automatically and respectively comparing the user feedback related to the manifested symptoms or manifested side effects within the predetermined parameters with the identified symptoms and identified side effects in order to respectively identify symptom matches or side effect matches;

iv. determining that an assigned dosage should be increased based on an efficacy score between (a) a presence of symptom matches, (b) an absence of side effect matches and (c) the discrepancy in (ii), stored in the memory of the controller; and v. determining that an assigned dosage should be decreased based on an efficacy score between (a) a presence of side effect matches, (b) an absence of symptom matches and (c) the discrepancy in (ii), stored in the memory of the controller; and automatically communicating in real-time the determined modification of the assigned dosage via the user interface.

2. A computer implemented system according to claim 1, wherein the information related to the plurality of previous target individuals further comprises identifiers associated with respective ones of the plurality of target individuals thereby providing previous identifiers.

3. A computer implemented system according to claim 2, wherein the computer implemented steps further comprise:

receiving information from the user interface regarding the target individual's identifiers and comparing this information to the previous identifiers to assess similarities therebetween thereby providing common identifiers;

identifying the previous target individuals with the common identifiers and with the matched condition and matched therapeutic composition thereby providing common previous target individuals;

identifying in real-time the symptoms of the common previous target individuals for the matched condition thereby providing common symptoms and identifying the side effects of the common previous target individuals for the matched therapeutic composition thereby providing common side effects;

prompting and receiving real-time user feedback via the user interface regarding the possibility of the target individual manifesting the common symptoms or the common side effects;

determining in real-time based on the user feedback whether the therapeutic composition assigned to the target individual is administered at a dosage that should be modified in order to be increased or decreased, wherein manifestation of common symptoms is indicative of a dosage that should be increased and manifestation of common side effects is indicative of a dosage that should be decreased.

4. A computer implemented system according to claim 1, wherein the database further comprises a plurality of predetermined posology ranges related to the administration of respective ones of the plurality of the therapeutic compositions for treating respective ones of the plurality of health conditions, wherein the computer implemented steps further comprise:

receiving information via the user interface regarding a prescribed posology for the target individual and comparing this information to the plurality of posology ranges for the matched therapeutic composition in treating the matched health condition thereby identifying a predetermined posology range for the target individual;

comparing in real-time the prescribed posology range with the predetermined posology range to identify discrepancies therebetween; and determining in real-time based on the user feedback and on the identified discrepancies whether the prescribed posology range should be modified to remove the identified discrepancies, wherein manifestation of identified symptoms or identified side effects is indicative of a prescribed posology range that should be modified.

5. A computer implemented system according to claim 4, wherein the database further comprises a databank of information related to a plurality of previous target individuals, wherein the information related to the plurality of previous target individuals comprises plurality of previous posology ranges related to the administration of respective ones of the plurality of the therapeutic compositions for treating respective ones of the plurality of health conditions.

6. A computer implemented system according to claim 5, wherein the memory of computer implemented steps further comprises statistically modifying the plurality of predetermined posology ranges in the database in accordance with the information related to the plurality of the previous target individuals.

7. A computer implemented system according claim 5, wherein the information related to the plurality of previous target individuals further comprises identifiers associated with respective ones of the plurality of target individuals thereby providing previous identifiers.

8. A computer implemented system according to claim 7, wherein the computer implemented steps further comprise:

receiving information from the user interface regarding the target individual's identifiers and comparing this information to the previous identifiers to assess similarities therebetween thereby providing common identifiers;

identifying the previous target individuals with the common identifiers and with the matched condition and matched therapeutic composition thereby providing common previous target individuals;

processing the posology ranges of the common previous target individuals to provide a statistically common posology range;

comparing the prescribed posology range with the statistically common posology range to identify discrepancies therebetween; and determining based on the user feedback and on the identified discrepancies whether the prescribed posology range should be modified to remove the identified discrepancies, wherein manifestation of identified symptoms or identified side effects is indicative of a prescribed posology range that should be modified.

9. A computer implemented system according to claim 1, wherein the computer implementable steps further comprise transmitting the determined modification to the user interface.

10. A computer implemented system according to claim 1, wherein the user interface is configured to be used by a user selected from the group consisting of: the target individual, one or more physician, one or more monitor and a combination thereof.

11. A computer implemented system according to claim 1, further comprising one or more additional user interfaces, wherein the one or more additional user interfaces are respectively configured to display predetermined information regarding the target individual as selectively programmed to be transmitted by the controller.

12. A computer implemented system according to claim 1, further comprising biosensors mounted to the target individual and in communication with the remote controller directly or via the user interface for providing in real-time the controller with information detected by the biosensors.

13. A computer implemented computer implemented system according to claim 12, wherein the information detected by the biosensors comprises: one or more symptoms, one or more side effects, one or more identifiers and a combination thereof.

* * * * *